United States Patent
Nose

(10) Patent No.: US 11,630,222 B2
(45) Date of Patent: Apr. 18, 2023

(54) COLLIMATOR MODULE, MEDICAL APPARATUS, AND METHOD OF MAKING COLLIMATOR MODULE

(71) Applicant: General Electric Company, Schenectady, NY (US)

(72) Inventor: Katsumasa Nose, Tokyo (JP)

(73) Assignee: General Electric Company, Schenectady, NY (US)

( * ) Notice: Subject to any disclaimer, the term of this patent is extended or adjusted under 35 U.S.C. 154(b) by 196 days.

(21) Appl. No.: 17/123,213

(22) Filed: Dec. 16, 2020

(65) Prior Publication Data
US 2021/0199820 A1 Jul. 1, 2021

(30) Foreign Application Priority Data

Dec. 25, 2019 (JP) .............................. JP2019-234388

(51) Int. Cl.
*G01T 1/29* (2006.01)
*G21K 1/02* (2006.01)
*G02B 27/30* (2006.01)
*A61B 6/00* (2006.01)

(52) U.S. Cl.
CPC ............ *G01T 1/295* (2013.01); *A61B 6/4291* (2013.01); *G02B 27/30* (2013.01); *G21K 1/025* (2013.01)

(58) Field of Classification Search
CPC ........ G01T 1/295; G21K 1/025; A61B 6/4291
See application file for complete search history.

(56) References Cited

U.S. PATENT DOCUMENTS

| 6,594,342 | B2* | 7/2003 | Castleberry ............ G21K 1/025 |
| | | | 901/17 |
| 8,861,685 | B2* | 10/2014 | Pohan ..................... G21K 1/025 |
| | | | 378/154 |
| 2015/0162107 | A1* | 6/2015 | Kato ....................... G21K 1/025 |
| | | | 156/60 |

FOREIGN PATENT DOCUMENTS

| JP | 2009-232955 A | 10/2009 | |
| JP | 2009232955 A | * 10/2009 | ............... A61B 6/03 |

* cited by examiner

*Primary Examiner* — David P Porta
*Assistant Examiner* — Jeremy S Valentiner

(57) ABSTRACT

To provide a technique with which it is possible to make collimator plates resistant to deformation, and reduce position offsets in the collimator plates, a collimator module (1) comprises a plurality of collimator plate sets (2) lined up side by side in a channel direction (CH), wherein each collimator plate set (2) comprises a first collimator plate (3), a second collimator plate (4), and a joint layer (5) disposed between the first collimator plate (3) and second collimator plate (4) for adhesively bonding the first collimator plate (3) and second collimator plate (4) together, and the plurality of collimator plate sets (2) are lined up side by side in the channel direction (CH) with an air layer (20) intervening between adjacent two of the plurality of collimator plate sets (2).

13 Claims, 31 Drawing Sheets

FIG. 12
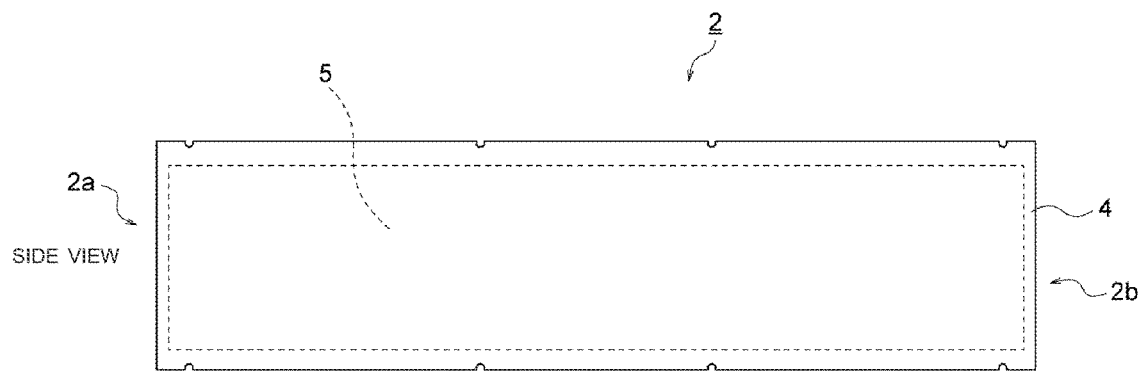
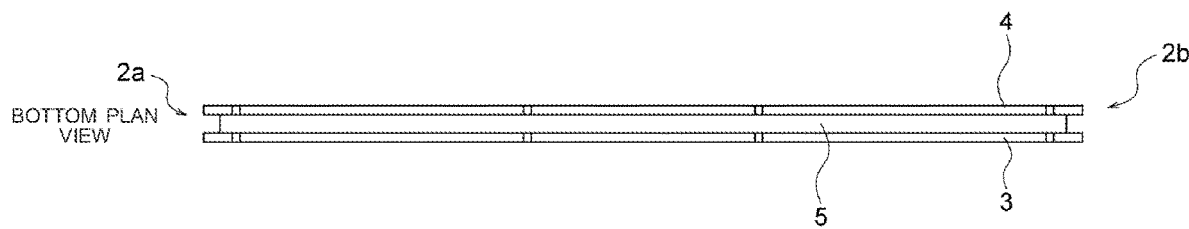

FIG. 19
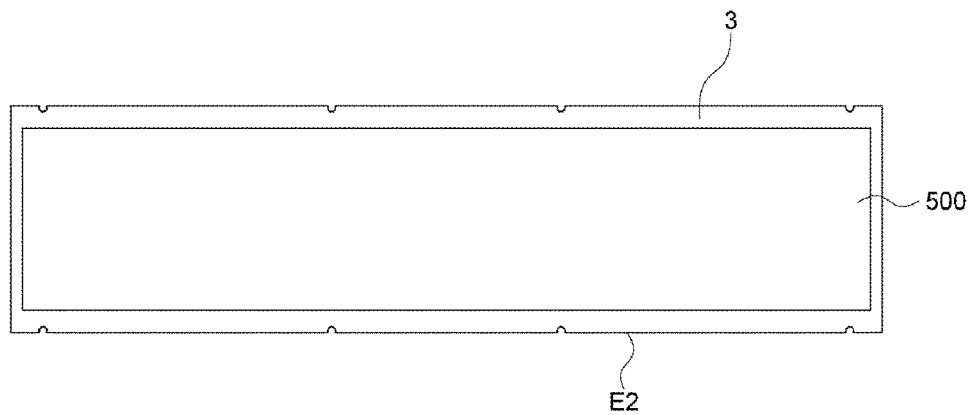
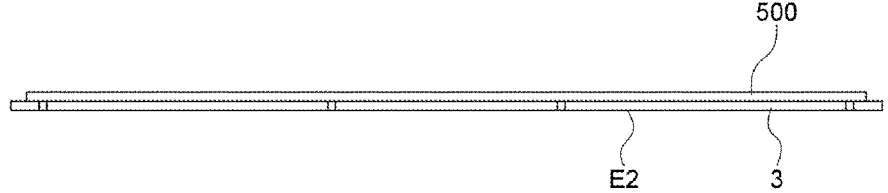

FIG. 26
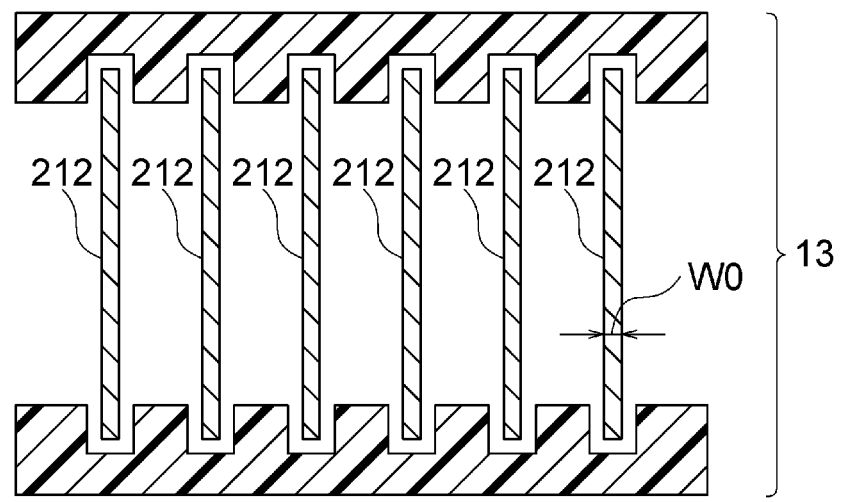
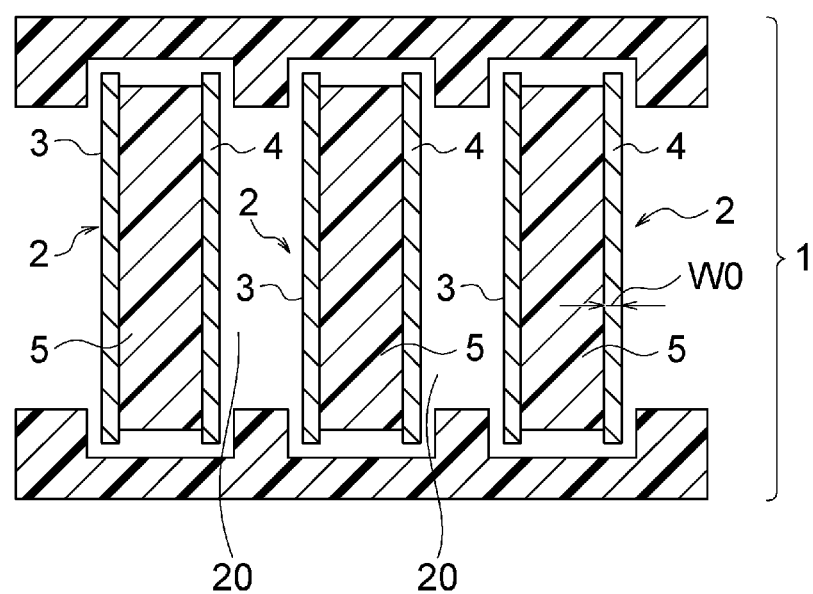

_US 11,630,222 B2_

COLLIMATOR MODULE, MEDICAL APPARATUS, AND METHOD OF MAKING COLLIMATOR MODULE

FIELD

The present invention relates to a collimator module having collimator plates, a medical apparatus having the collimator module, and a method of making the collimator module.

BACKGROUND

There have been X-ray CT apparatuses known as apparatuses for non-invasively imaging a patient. The X-ray CT apparatuses are installed in various medical institutions because of their ability to acquire images of a patient in a short period of time.

An X-ray CT apparatus has an X-ray tube, an X-ray detection apparatus, and a DAS (data acquisition system). X-rays output from the X-ray tube pass through a patient, and are detected at the X-ray detection apparatus. The DAS converts the detected X-rays into X-ray projection data, and acquires them. A CT image is reconstructed based on the X-ray projection data acquire by the DAS.

The X-ray detection apparatus has an X-ray detector for detecting the X-rays having passed through the patient. The X-ray detection apparatus moreover has a collimator aligned to the X-ray detector on a side of X-ray entrance of the X-ray detector. The collimator is provided for removing scattered X-rays, and a variety of collimators have been developed.
Patent Document 1: Gazette of Japanese Patent Application KOKAI No. 2009-232955

A collimator generally has a plurality of collimator modules. Now an example of the collimator module will be described hereinbelow.

FIG. 1 is a schematic cross-sectional view of part of a collimator module 11. The collimator module 11 has a plurality of collimator plates 21 lined up side by side in a channel direction CH. Here are shown three collimator plates 21 for convenience of explanation. The collimator plates 21 are provided on their upper and lower portions with reinforcing plates 22 and 23 for enhancing rigidity of the collimator module 11 itself. The reinforcing plates 22 and 23 have grooves 22a and 23a, respectively, for receiving the collimator plates 21. Below the collimator module 11 are shown an X-ray detector 240. The X-ray detector 240 has a plurality of detector elements 241 lined up side by side in the channel direction CH at intervals of P1. In FIG. 1, X-rays emitted from an X-ray tube (not shown) enter the collimator module 11 from the side of the reinforcing plate 22. Each collimator plate 21 is provided along a direction of X-ray emission.

Since each collimator plate 21 is provided along the direction of X-ray emission as described above, these collimator plates 21 are not exactly parallel with one another. In the drawings used in the present application, however, they are shown as if they were parallel with one another for convenience of explanation. In FIG. 1, an interval between adjacent collimator plates 21 is designated as symbol "P0" with reference to their center positions in the direction of X-ray emission.

The X-rays pass through the collimator module 11 to reach the detector elements 241. Thus, the X-rays having passed through the patient can be detected.

In imaging a patient by the X-ray CT apparatus, it is necessary to rotate the rotating section of the gantry. Therefore, a centrifugal force caused by the rotation of the rotating section acts on the collimator plates 21, which becomes a cause of their deformation. Since a significant deformation of the collimator plates 21 results in artifacts, it is desirable that the collimator plates 21 have as much rigidity as possible so as to prevent deformation under the centrifugal force as much as possible.

On the other hand, in recent years, to obtain a high-resolution image by the X-ray CT apparatus, the pixel size in a detector is becoming increasingly smaller. Now consider an idea that the interval P1 between the detector elements 241 in the channel direction CH is halved from that shown in FIG. 1 to reduce the pixel size in the detector.

FIG. 2 is a diagram showing the collimator module in which the intervals between the detector elements are approximately halved.

FIG. 2 shows in its upper portion the X-ray detector 240 and collimator module 11 shown in FIG. 1. On the other hand, it shows in its lower portion an X-ray detector 240 having a plurality of detector elements 24 lined up side by side at intervals of P3 (=P1/2), a half of the interval P1 between the detector elements 241 shown in the upper portion of FIG. 2, and a collimator module 12 aligned to the X-ray detector 240.

The collimator module 12 shown in the lower portion of FIG. 2 has a plurality of collimator plates 211. The collimator plates 211 have the same structure as the collimator plates 21. In the collimator module 12, however, the interval P3 between the detector elements 24 is halved from the interval P1 between the detector elements 241, and accordingly, the collimator plates 211 are lined up side by side in the channel direction CH at intervals of P2, a half of the interval P0 between the collimator plates 21.

Therefore, while the collimator plates 211 in the collimator module 12 in FIG. 2 each have the same width w as the collimator plates 21, they line up side by side at intervals of P2, a half of the interval P0 between the collimator plates 21. Thus, the proportion of X-rays blocked by the collimator plates 211 is higher than that blocked by the collimator plates 21, resulting in a problem that use of the collimator module 12 lowers X-ray use efficiency.

Therefore, when the interval between detector elements is reduced (the size of a detector element is reduced), it is necessary to reduce the thickness of the collimator plate 211 in order to restrain the lowering of X-ray use efficiency (see FIG. 3).

FIG. 3 is a diagram showing an example in which the thickness of the collimator plates is reduced.

FIG. 3 shows in its upper portion the same collimator module 11 as that in the upper portion of FIG. 2. On the other hand, it shows in its lower portion a collimator module 13 having collimator plates 212 thinner than the collimator plates 211 shown in FIG. 2.

The collimator plates 212 in the collimator module 13 shown in the lower portion of FIG. 3 are formed to have a thickness w0 smaller than the thickness w of the collimator plate 21 shown in the upper portion of FIG. 3. Lowering of X-ray use efficiency can thus be restrained. However, thinner collimator plates have lowered rigidity. This poses a problem that when the rotating section of the gantry rotates, the collimator plates 212 become vulnerable to deformation due to a centrifugal force acting on them.

Moreover, in assembling a collimator module, it is necessary to use an assembly jig to align the collimator plates. However, since the thinner collimator plates are vulnerable to deformation, there is a problem that it becomes difficult to align the collimator plates at desired positions.

On the other hand, Patent Document 1 discloses collimator plates 505 filled in their spaces with a foam material 509 to secure a degree of flatness of the collimator plates 505 (see Paragraph [0046] in the cited reference 1). The foam material 509, however, thermally expands depending upon the surrounding temperature environment. Thermal expansion of the foam material 509 results in accumulation of its thermally expanded volume in the channel direction, posing a problem that the position offset in the collimator plates 505 becomes larger.

Therefore, there is a need for a technique with which collimator plates can be made resistant to deformation, and the position offset in the collimator plates can be reduced.

SUMMARY

This summary introduces concepts that are described in more detail in the detailed description. It should not be used to identify essential features of the claimed subject matter, nor to limit the scope of the claimed subject matter.

The present invention, in its first aspect, is a collimator module comprising a plurality of collimator plate sets lined up side by side in a specific direction, wherein
  each collimator plate set comprises:
  a first collimator plate;
  a second collimator plate; and
  a joint layer disposed between said first collimator plate and said second collimator plate for joining said first collimator plate and said second collimator plate together, and
said plurality of collimator plate sets are lined up side by side in said specific direction with an air layer intervening between adjacent two of said plurality of collimator plate sets.

The present invention, in its second aspect, is a radiation detection apparatus having a plurality of collimator modules disposed on a side of radiation entrance of a detector,
  each collimator module comprising a plurality of collimator plate sets lined up side by side in a specific direction, wherein
  each collimator plate set comprises:
  a first collimator plate;
  a second collimator plate; and
  a joint layer disposed between said first collimator plate and said second collimator plate for joining said first collimator plate and said second collimator plate together, and
said plurality of collimator plate sets are lined up side by side in said specific direction with an air layer intervening between adjacent two of said plurality of collimator plate sets.

The present invention, in its third aspect, is a method of making a collimator module comprising a plurality of collimator plate sets, comprising:
  making said plurality of collimator plate sets, each collimator plate set comprising: a first collimator plate; a second collimator plate; and a joint layer disposed between said first collimator plate and said second collimator plate for joining said first collimator plate and said second collimator plate together, and
  inserting said plurality of collimator plate sets into slots in brackets with an air layer intervening between adjacent two of said plurality of collimator plate sets.

A first collimator plate and a second collimator plate are joined together by a joint layer. Therefore, the joint layer and first and second collimator plates can synergically provide a collimator plate set having enhanced rigidity as a whole. Thus, the first and second collimator plates can be made resistant to deformation.

Moreover, an air layer intervenes between adjacent collimator plate sets. Since the adjacent collimator plate sets are thus held in a non-contact manner, accumulation of the position offset in the collimator plate sets in a direction of lining-up of the collimator plate sets can be prevented even when the joint layers in the collimator plate sets thermally expand. Therefore, it is possible to reduce the position offset in the collimator plates.

BRIEF DESCRIPTION OF THE DRAWINGS

FIG. 12 is a side view and a bottom plan view of the collimator plate set 2.

FIG. 19 is a side view and a bottom plan view of the collimator plate 3 and bonding sheet 500 shown in FIG. 18.

FIG. 26 is an explanatory diagram for an effect of the collimator module 1 having joint layers 5.

DETAILED DESCRIPTION

Embodiments of the present disclosure will now be described, by way of example, with reference to the Figures.

Figure 4:
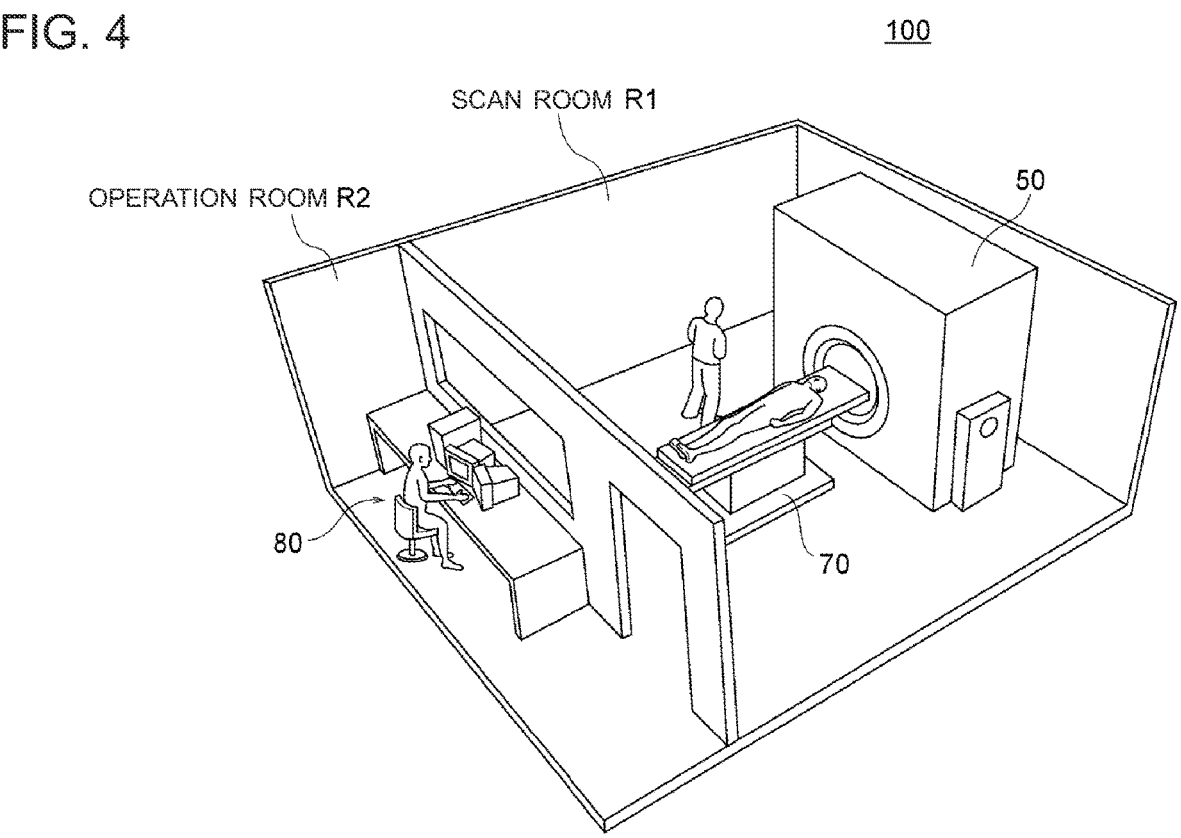
FIG. 4 is an external view of an X-ray CT apparatus in the present embodiment.

FIG. 4 is an external view of an X-ray CT apparatus in an embodiment.

An X-ray CT apparatus 100 comprises a gantry 50, a table 70, and an operation console 80.

The gantry 50 and table 70 are installed in a scan room R1, while the operation console 80 is installed in an operation room R2.

Figure 5:
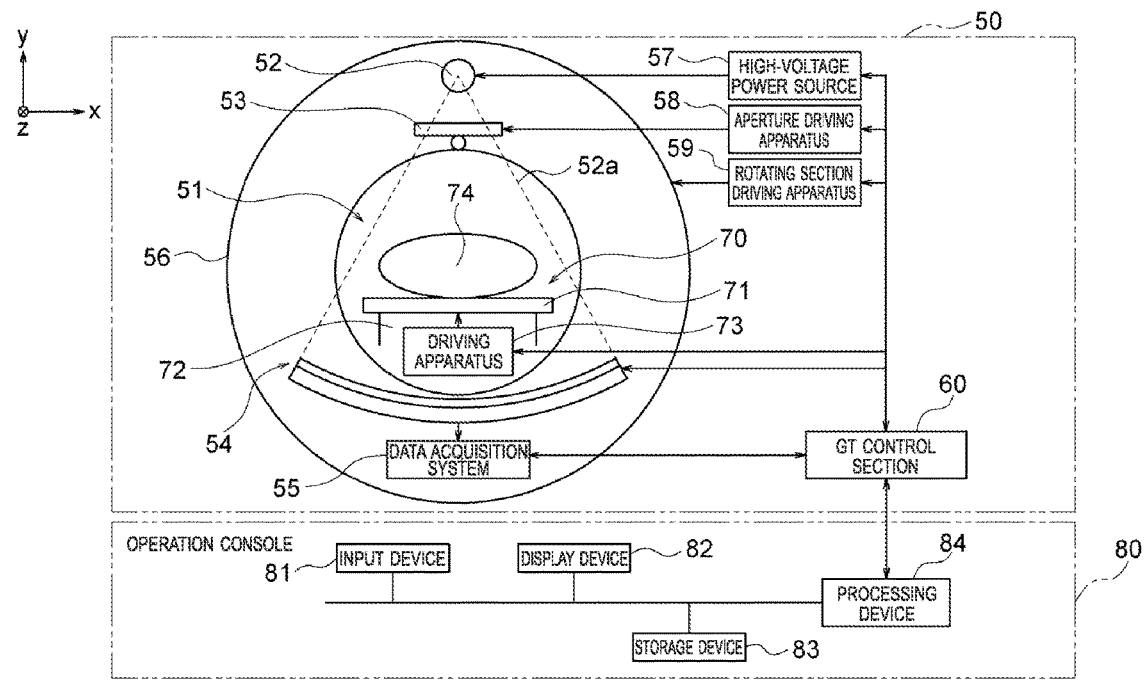
FIG. 5 is a block diagram of the X-ray CT apparatus 100 in the present embodiment.

FIG. 5 is a block diagram of the X-ray CT apparatus 100 in the present embodiment.

The operation console 80 has an input device 81, a display device 82, a storage device 83, a processing device 84, etc.

The input device 81 comprises a keyboard, a pointing device, etc. for accepting an operator's input of a command and/or information, and performing several kinds of operations. The display device 82 is for displaying visual information such as images, etc., and is, for example, an LCD (Liquid Crystal Display), an organic EL (Electro-Luminescence) display, or the like.

The storage device 83 stores therein programs, data, etc. The storage device 83 is an HDD (Hard Disk Drive), and semiconductor memory, such as RAM (Random Access Memory) and ROM (Read Only Memory). The storage device 83 may include a portable storage medium, such as a CD (Compact Disk), a DVD (Digital Versatile Disk), or the like.

The processing device 84 is for performing image reconstruction processing based on data for a patient 74 acquired with the gantry 50, and performing several other kinds of computations. The device 84 may be constructed using processors.

The table 70 has a cradle 71, a cradle support base 72, and a driving apparatus 73. The cradle 71 is for supporting the patient 74, an object of imaging. The cradle support base 72 is for supporting the cradle 71 movably in y- and z-directions. The driving apparatus 73 is for driving the cradle 71 and cradle support base 72. Next, the gantry 50 will be described.

The gantry 50 has a bore 51 for forming space through which the patient 74 can be moved.

The gantry 50 also has an X-ray tube 52, an aperture 53, an X-ray detection apparatus 54, a data acquisition system 55, a rotating section 56, a high-voltage power source 57, an aperture driving apparatus 58, a rotating section driving apparatus 59, a GT (Gantry Table) control section 60, etc.

The X-ray tube 52, aperture 53, X-ray detection apparatus 54, and data acquisition system 55 are mounted on the rotating section 56.

The X-ray tube 52 and X-ray detection apparatus 54 are disposed facing each other sandwiching the bore 51 of the gantry 50.

The aperture 53 is disposed between the X-ray tube 52 and bore 51. The aperture 53 shapes X-rays emitted from an X-ray focus of the X-ray tube 52 toward the X-ray detection apparatus 54 into a fan beam or a cone beam.

The X-ray detection apparatus 54 detects X-rays having passed through the patient 74. The data acquisition system (DAS) 55 converts the detected X-rays into X-ray projection data, and acquires them. The X-ray detection apparatus 54 will be described in detail later.

The high-voltage power source 57 supplies high voltage and electric current to the X-ray tube 52.

The aperture driving apparatus 58 drives the aperture 53 to modify the shape of its opening.

The rotating section driving apparatus 59 rotationally drives the rotating section 56.

The GT control section 60 controls several apparatuses and sections in the gantry 50, the driving apparatus 73, etc.

When the rotating section driving apparatus 59 rotates the rotating section 56, the X-ray tube 52 and X-ray detection apparatus 54 rotate around the patient 74. The fan- or cone-beam X-rays 52a, which are emitted from the X-ray tube 52 and shaped by the aperture 53, pass through the patient 74 to reach a detection surface of the X-ray detection apparatus 54. A direction of an extent of the fan-beam or cone-beam X-rays 52a in the xy-plane will be referred to herein as channel direction; a direction of an extent thereof in the z-direction or the z-direction per se will be referred to herein as slice direction. Moreover, a direction in which the X-rays are emitted from the X-ray tube 52 will be referred to herein as direction of X-ray emission.

Next, the X-ray detection apparatus 54 will be described.

Figure 6:
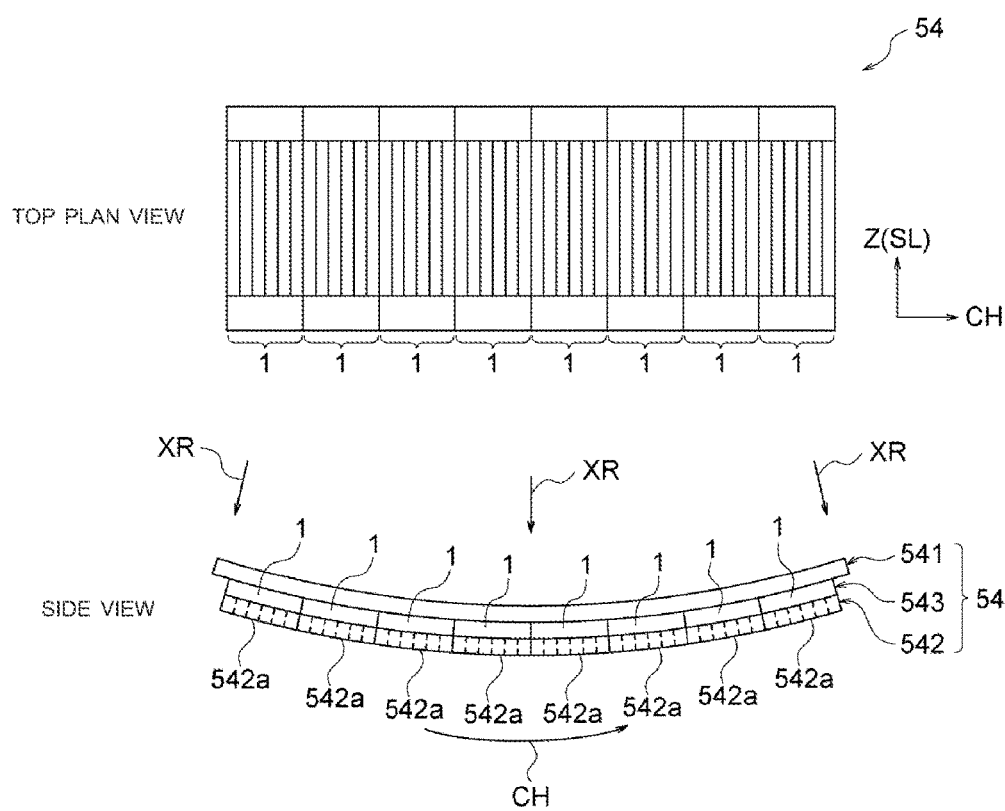
FIG. 6 is a diagram showing a configuration of the X-ray detecting apparatus 54.

FIG. 6 is a diagram showing a configuration of the X-ray detecting apparatus 54. FIG. 6 shows in its upper portion a top plan view of the X-ray detection apparatus 54, and in its lower portion a view (side view) of the X-ray detection apparatus 54 as viewed in the slice direction SL.

As shown in FIG. 6, the X-ray detection apparatus 54 comprises a frame 541, and an X-ray detector 542 and a collimator apparatus 543 attached to the frame 541.

The X-ray detector 542 has a plurality of detector modules 542a arranged in an array in the channel direction CH. The detector modules 542a each have a plurality of detector elements arranged in a matrix in the channel direction CH and slice direction SL.

These detector elements detect X-rays.

The collimator apparatus 543 is disposed on a side of X-ray entrance of the X-ray detector 542, for removing scattered X-rays. The collimator apparatus 543 has a plurality of collimator modules 1 arranged in an array in the channel direction CH, and each collimator module 1 is disposed on the side of X-ray entrance of the X-ray detector 542.

Now a configuration of the collimator module 1 will be described hereinbelow.

FIGS. 7 to 10 are explanatory views of a configuration of the collimator module 1.

Figure 7:
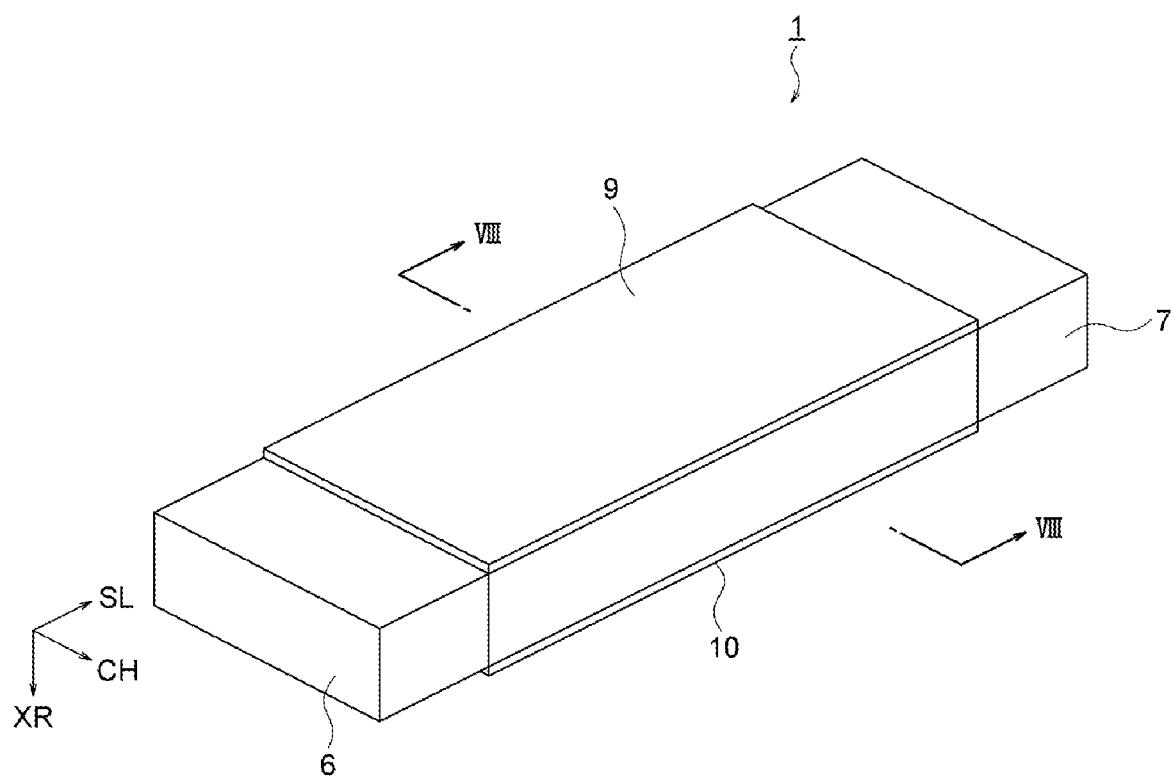
FIG. 7 is a perspective view of a collimator module 1.
Figure 8:
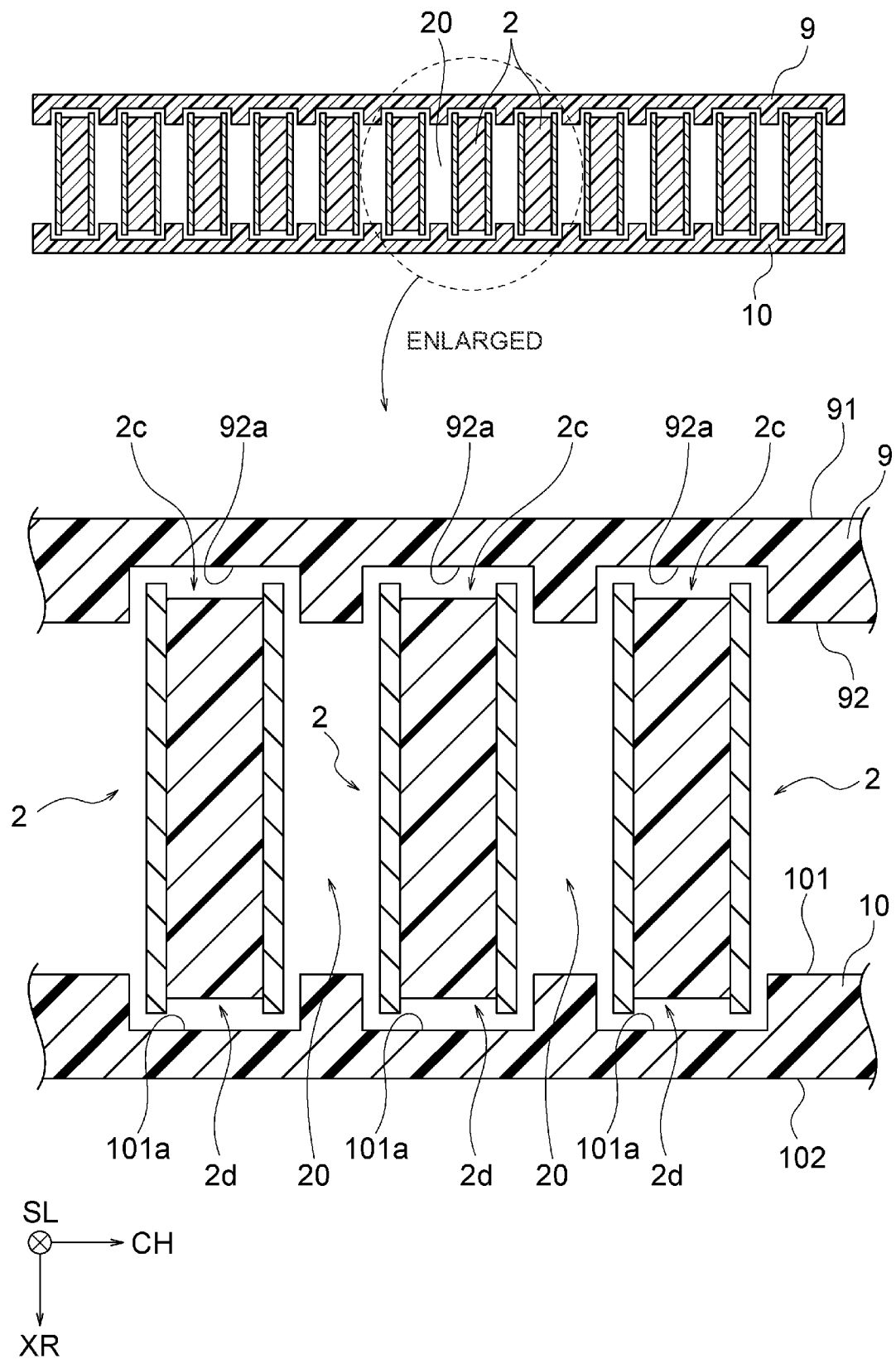
FIG. 8 is an VIII-VIII cross-sectional view of the collimator module 1.
Figure 9:
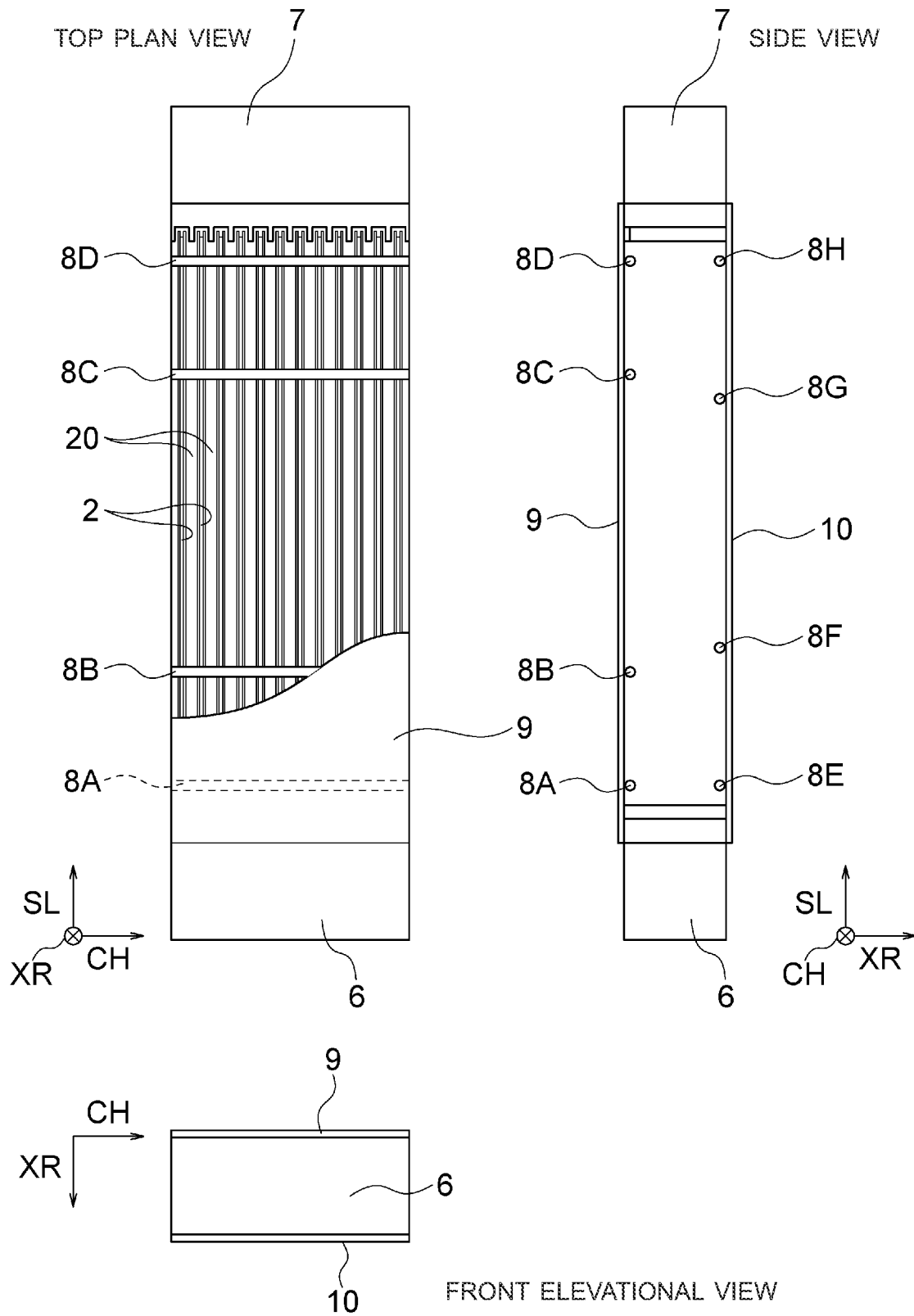
FIG. 9 is a top plan view, a side view, and a front elevational view of the collimator module 1.
Figure 10:
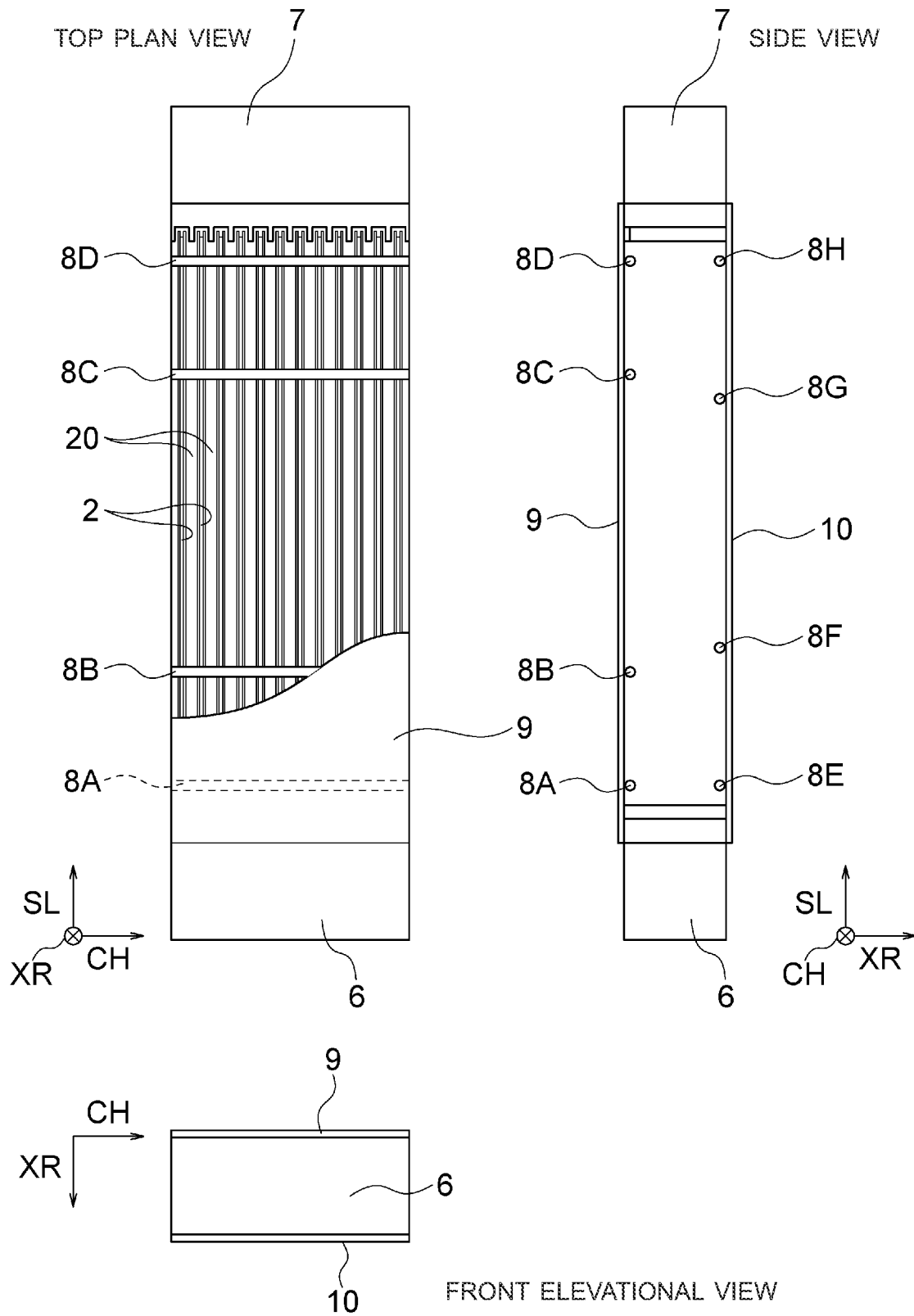
FIG. 10 is an exploded perspective view of the collimator module 1.

FIG. 7 is a perspective view, FIG. 8 is a VIII-VIII cross-sectional view, FIG. 9 is a top plan view, a side view, and a front elevational view, and FIG. 10 is an exploded perspective view, of the collimator module 1. In the top plan view of the collimator module 1 in FIG. 9, only part of the member designated by Symbol 9 is shown in order to show internal components of the collimator module 1. Note that only main portions of the configuration are shown in the drawings here. Moreover, it should be noted that the drawings show features of the configuration with exaggeration, and the structures, sizes, and numbers thereof are different from the actual ones.

As shown in FIG. 10, the collimator module 1 has a plurality of collimator plate sets 2, a pair of (two) brackets 6 and 7, four upper fixing rods 8A to 8D, four lower fixing rods 8E to 8H, one upper reinforcing plate 9, and one lower reinforcing plate 10.

First, a collimator plate set 2 will be described referring to FIGS. 11 to 15.

Figure 11:
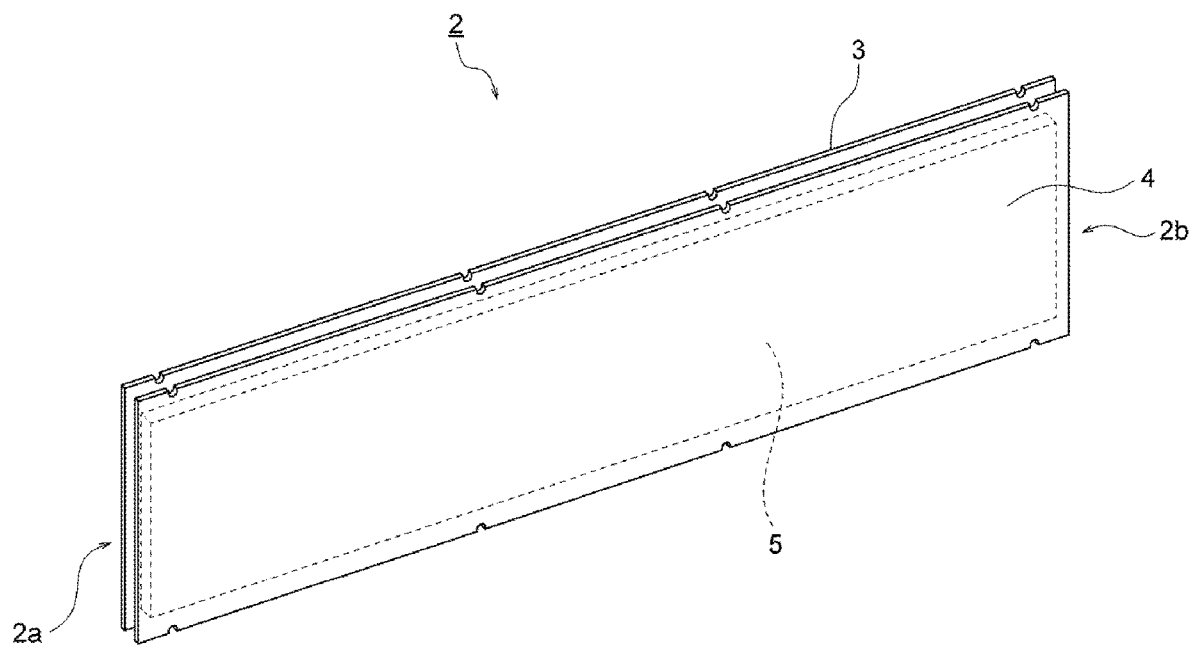
FIG. 11 is a perspective view of a collimator plate set 2.
Figure 13:
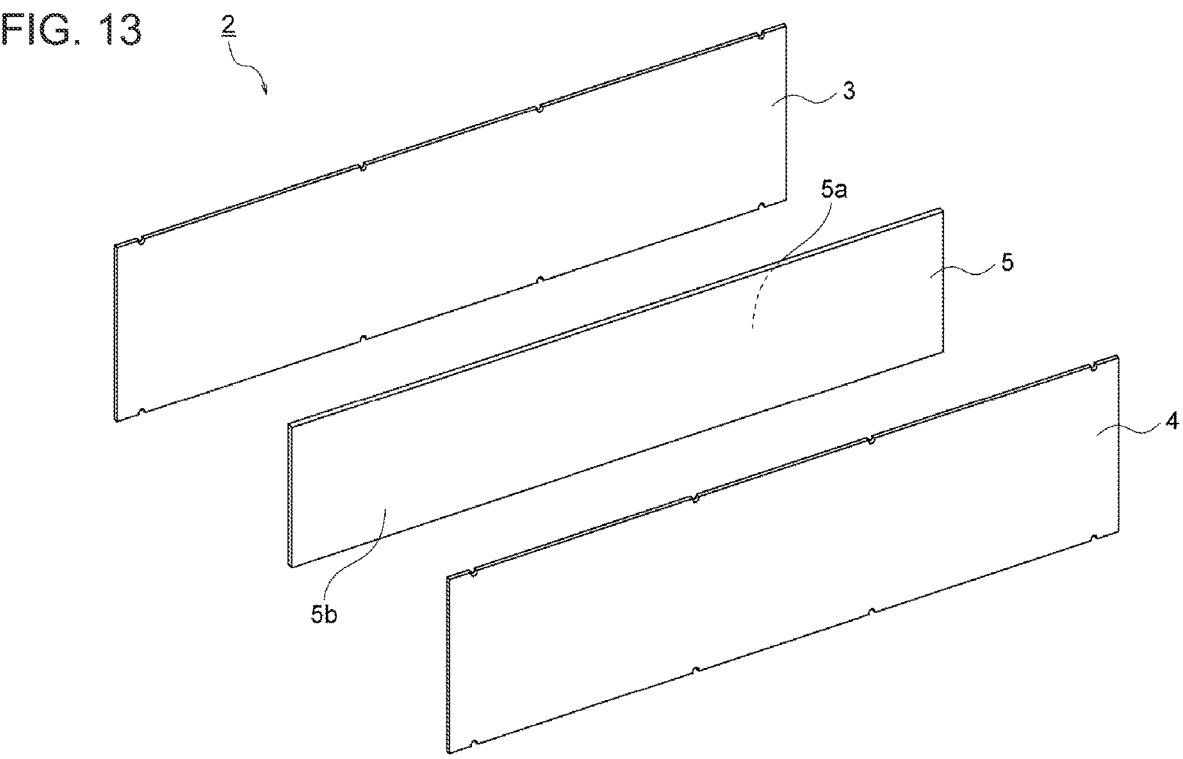
FIG. 13 is an exploded perspective view of the collimator plate set 2.

FIG. 11 is a perspective view, FIG. 12 is a side view and a bottom plan view, and FIG. 13 is an exploded perspective view, of the collimator plate set 2.

The collimator plate set 2 has two collimator plates 3 and 4, and a joint layer 5.

Figure 14:
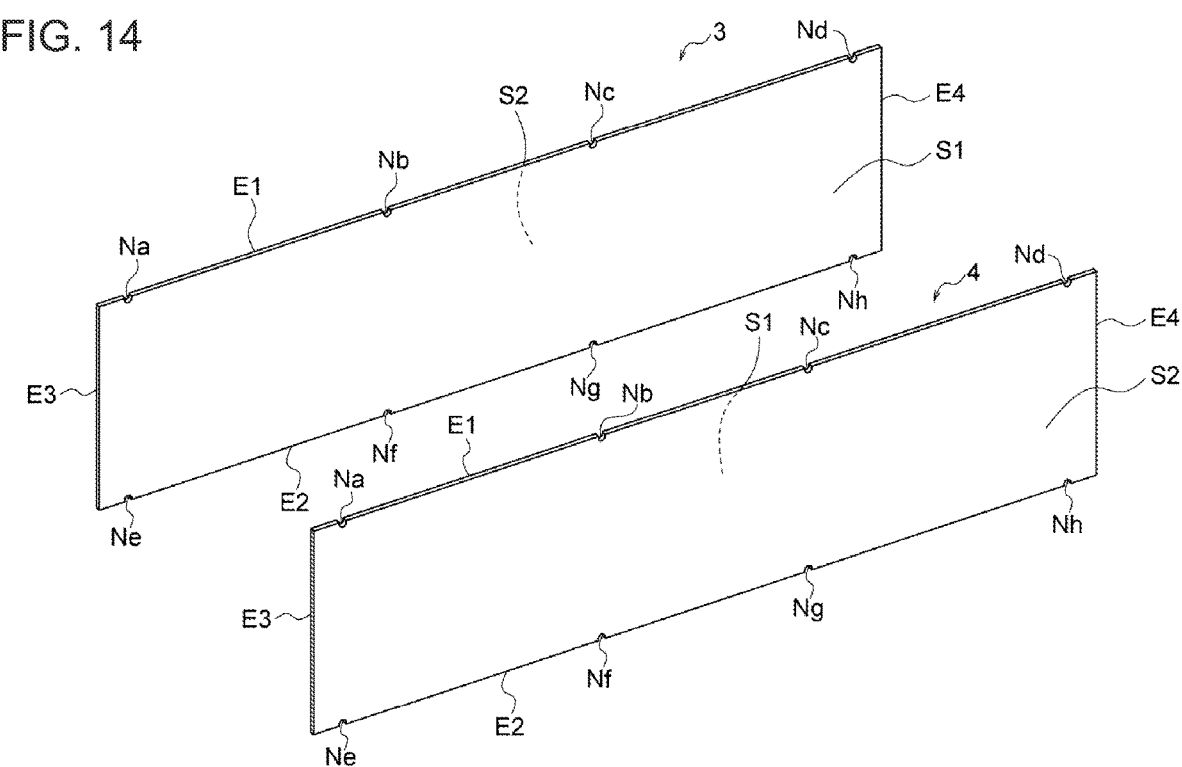
FIG. 14 is a perspective view of the collimator plates 3 and 4.
Figure 15:
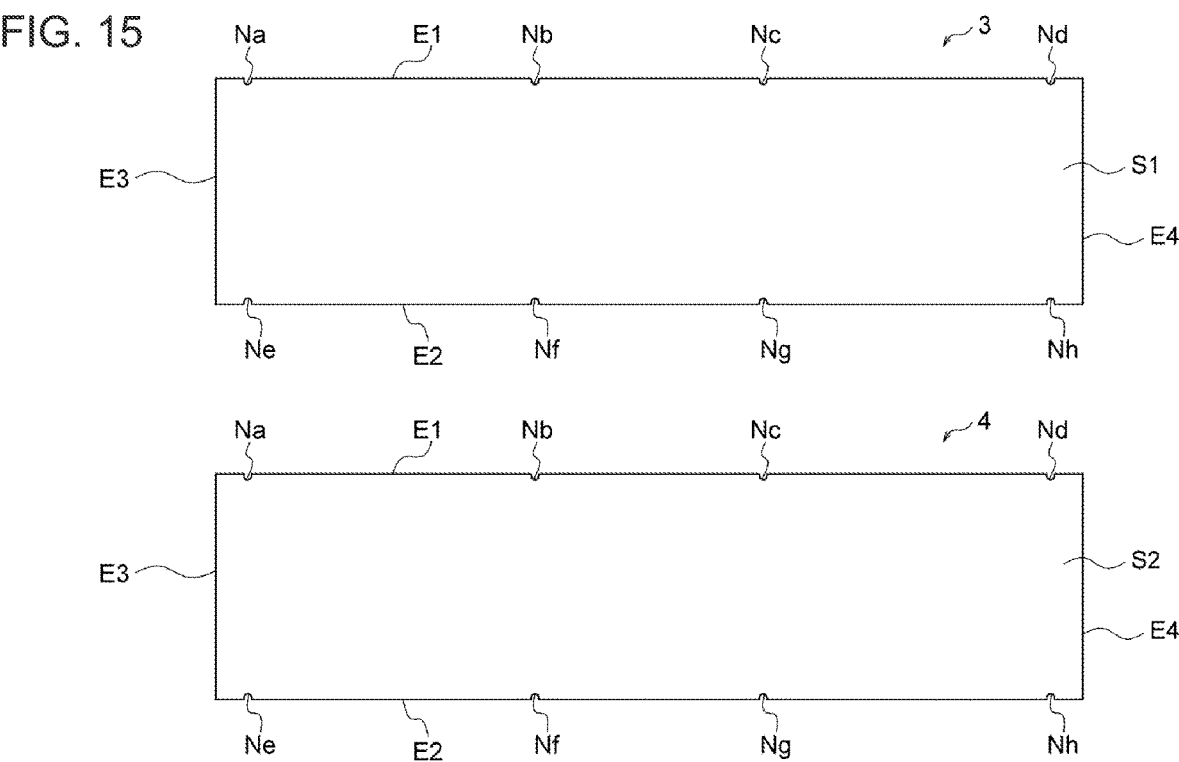
FIG. 15 is a side view of the collimator plates 3 and 4.

FIGS. 14 and 15 are explanatory views of the collimator plates 3 and 4.

FIG. 14 is a perspective view and FIG. 15 is a side view of the collimator plates 3 and 4.

The collimator plates 3 and 4 are for removing scattered X-rays. The collimator plates 3 and 4 are made using an X-ray shielding material, i.e., highly X-ray absorptive material, for example, tungsten, molybdenum, or the like. The collimator plates 3 and 4 both have the same material and the same shape, except deviations in manufacture/processing.

The collimator plate 3 has a first surface S1, and a second surface S2 facing in a direction opposite to the first surface S1. The first surface S1 is a surface joined to the joint layer 5 (see FIG. 13), while the second surface S2 is a surface to which the joint layer 5 is not joined. The first surface S1 and second surface S2 have a generally rectangular shape.

The collimator plate 3 also has an upper edge E1 and a lower edge E2 extending along long sides of the first surface S1 (and second surface S2), and a front edge E3 and a rear edge E4 extending along short sides of the first surface S1 (and second surface S2).

The collimator plate 3 is formed on its upper edge E1 with four notches Na to Nd. The four notches Na to Nd are formed at positions generally horizontally symmetric with respect to a center of the upper edge E1 in its longitudinal direction. Likewise, the collimator plate 3 is formed on its lower edge E2 with four notches Ne to Nh. The four notches Ne to Nh are formed at positions generally horizontally symmetric with respect to a center of the lower edge E2 in its longitudinal direction. While the notches Ne to Nh are arc-shaped, for example, they may have a rectangular or wedge-like shape (V shape), or the like.

The plate thickness of the collimator plate 3 may have a value of several tens of micrometers, for example. The width of each of the notches Na to Nh may have a value within a range of from 300 to 500 micrometers, for example.

The collimator plate 3 is thus constructed as described above. It should be noted that the other collimator plate 4 has the same structure as the collimator plate 3, except that the positional relationship between the first surface S1 to which the joint layer 5 is joined, and the second surface S2 to which the joint layer 5 is not joined is reversed.

Next, the joint layer 5 will be described referring to FIG. 13. The joint layer 5 has a bonding surface 5a to which the collimator plate is adhesively bonded, and a bonding surface 5b to which the collimator plate 4 is adhesively bonded. The joint layer 5 is disposed between the collimator plates 3 and 4 for joining them together.

The collimator plate set 2 has the collimator plate 3, collimator plate 4, and joint layer 5 constructed as described above.

The collimator module 1 has a plurality of the thus-constructed collimator plate sets 2. The plurality of collimator plate sets 2 are arranged to line up side by side in the channel direction CH, as shown in FIGS. 8 to 10, and further, an air layer 20 (see FIG. 8) intervenes between the adjacent collimator plate sets 2.

The collimator plate sets 2 are held by the brackets 6 and 7. Next, the brackets 6 and 7 will be described. The brackets 6 and 7 will be described referring to FIGS. 7 to 10 (mainly FIG. 10).

The pair of brackets 6 and 7 are constructed from a high-rigid, light-weight, and easy-to-process material, for example, an aluminum alloy, or the like. The pair of brackets 6 and 7 have generally horizontally symmetric shapes in the slice direction SL. The pair of brackets 6 and 7 are generally rectangular parallelepiped members.

The bracket 6 is formed on its surface 6a facing the collimator plate sets 2 with slots 6b in the same number as the number of the collimator plate sets 2 provided in the collimator module 1. Each of the plurality of slots 6b is formed to be able to receive a front end portion 2a of a corresponding collimator plate set 2. It should be noted that the bracket 6 is provided on its upper surface with an alignment pin (not shown) for aligning the collimator module 1 to the frame 541 (see FIG. 6).

On the other hand, the bracket 7 has a shape generally horizontally symmetric to the bracket 6 in the slice direction SL. The bracket 7 is formed on its surface 7a facing the collimator plate set 2 with slots 7b in the same number as the number of the collimator plate sets 2 provided in the collimator module 1. Each of the plurality of slots 7b is formed to be able to receive a rear end portion 2b of a corresponding collimator plate set 2. It should be noted that the bracket 7 is provided on its upper surface with an alignment pin (not shown) for aligning the collimator module 1 to the frame 541 (see FIG. 6), similarly to the bracket 6.

The brackets 6 and 7 are thus constructed as described above.

The brackets 6 and 7 hold the plurality of collimator plate sets 2 so that an air layer 20 intervenes between the adjacent collimator plate sets 2.

The collimator module 1 may be aligned to the frame 541 by inserting the alignment pins provided in the brackets 6 and 7 into holes (not shown) formed in the frame 541 of the X-ray detection apparatus 54.

Next, the upper fixing rods 8A to 8D and lower fixing rods 8E to 8H will be described. The upper fixing rods 8A to 8D and lower fixing rods 8E to 8H will be described mainly referring to FIG. 10.

The upper fixing rods 8A to 8D and lower fixing rods 8E to 8H are rods used for fixing the plurality of collimator plate sets 2.

The upper fixing rods 8A to 8D and lower fixing rods 8E to 8H are constructed from an X-ray transparent and relatively high-rigid material, for example, carbon. The upper fixing rods 8A to 8D and lower fixing rods 8E to 8H have a rod shape extending in the channel direction CH. These upper fixing rods 8A to 8D and lower fixing rods 8E to 8H each have an axial cross section of a circle, for example, although it may be a rectangle, polygon, ellipse, or the like. The upper fixing rods 8A, 8B, 8C, and 8D are received in the notches Na, Nb, Nc, and Nd, respectively, in the collimator plate sets 2, and are fixed to respective upper end portions 2c of the plurality of collimator plate sets 2 by an adhesive. Likewise, the lower fixing rods 8E, 8F, 8G, and 8H are received in the notches Ne, Nf, Ng, and Nh, respectively, in the collimator plate sets 2, and are fixed to respective lower end portions 2d of the plurality of collimator plate sets 2 by an adhesive. These upper fixing rods 8A to 8D and lower fixing rods 8E to 8H have a length in the channel direction CH approximately the same as the width of the brackets 6 and 7 in the channel direction CH. These upper fixing rods 8A to 8D and lower fixing rods 8E to 8H are moreover formed to have a width of their axial cross sections somewhat smaller than the width of the notches.

Next, the upper reinforcing plate 9 and lower reinforcing plate 10 will be described. The upper reinforcing plate 9 and lower reinforcing plate 10 will be described referring to FIGS. 7 to 10 (especially FIGS. 8 and 10).

The upper reinforcing plate 9 and lower reinforcing plate 10 are for enhancing rigidity of the collimator module. The upper reinforcing plate 9 and lower reinforcing plate 10 are constructed from an X-ray transparent and relatively high-rigid material, for example, a carbon resin such as carbon-fiber reinforced plastics (CFRP). The upper reinforcing plate 9 and lower reinforcing plate 10 have a generally or substantially rectangular parallelepiped shape.

The upper reinforcing plate 9 has an upper surface 91 and a lower surface 92, as shown in FIG. 8. The lower surface 92 is a surface covering the upper end portion 2c of each of the plurality of collimator plate sets 2. The lower surface 92 is formed with a plurality of grooves 92a. The number of the grooves 92a formed in the lower surface 92 may be the same as that of the collimator plate sets 2 provided in the collimator module 1. Each of the plurality of grooves 92a is for inserting therein the upper end portion 2c of a corresponding one of the plurality of collimator plate sets 2. The plurality of grooves 92a are formed to line up side by side in the channel direction CH. Moreover, each groove 92a is formed to have a width in the channel direction CH and to extend in the slice direction SL. The width of the groove 92a in the channel direction CH is somewhat larger than the thickness of the collimator plate set 2, and may be set to a value within a range of several hundreds of micrometers, for example.

The lower reinforcing plate 10 has an upper surface 101 and a lower surface 102. The upper surface 101 is a surface covering the lower end portion 2d of each of the plurality of collimator plate sets 2. The upper surface 101 is formed with a plurality of grooves 101a. The number of the grooves 101a formed in the upper surface 101 may be the same as that of the collimator plate sets 2 provided in the collimator module 1. Each of the plurality of grooves 101a is for inserting therein the lower end portion 2d of a corresponding one of the plurality of collimator plate sets 2. The plurality of grooves 101a are formed to line up side by side in the channel direction CH. Moreover, each groove 101a is formed to have a width in the channel direction CH and to extend in the slice direction SL. The width of the groove 101a in the channel direction CH is somewhat larger than the thickness of the collimator plate set 2, and may be set to a value within a range of several hundreds of micrometers, for example, similarly to the groove 92a.

The upper reinforcing plate 9 is fixed to the plurality of collimator plate sets 2 and the pair of brackets 6 and 7 by an adhesive with the upper end portions 2c of the plurality of collimator plate sets 2 inserted into the plurality of grooves 92a. Likewise, the lower reinforcing plate 10 is fixed to the plurality of collimator plate sets 2 and the pair of brackets 6 and 7 by an adhesive with the lower end portions 2d of the plurality of collimator plate sets 2 inserted into the plurality of grooves 101a.

The collimator module 1 has the thus-constructed plurality of collimator plate sets 2, brackets 6 and 7, upper fixing rods 8A to 8D and lower fixing rods 8E to 8H, and upper reinforcing plate 9 and lower reinforcing plate 10.

Next, an example of a method of making the collimator module 1 will be described referring to FIG. 16.

Figure 16:
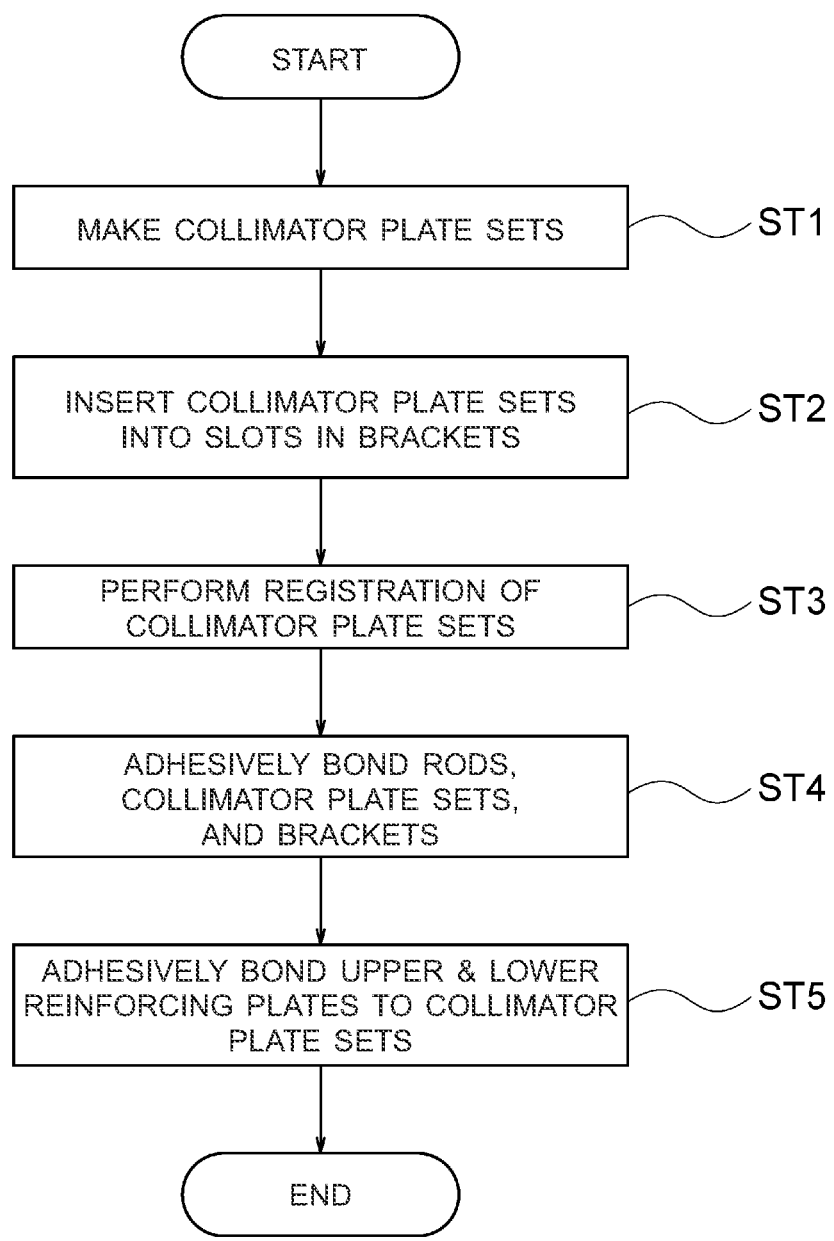
FIG. 16 is a flow chart of an example of a method of making the collimator module 1.

FIG. 16 is a flow chart of the example of the method of making the collimator module 1. Each of Steps ST1 to ST5 will now be described in turn.

At Step ST1, the plurality of collimator plate sets 2 are made. An example of a method of making the collimator plate set 2 will be described referring to FIGS. 17 to 23.

Figure 17:
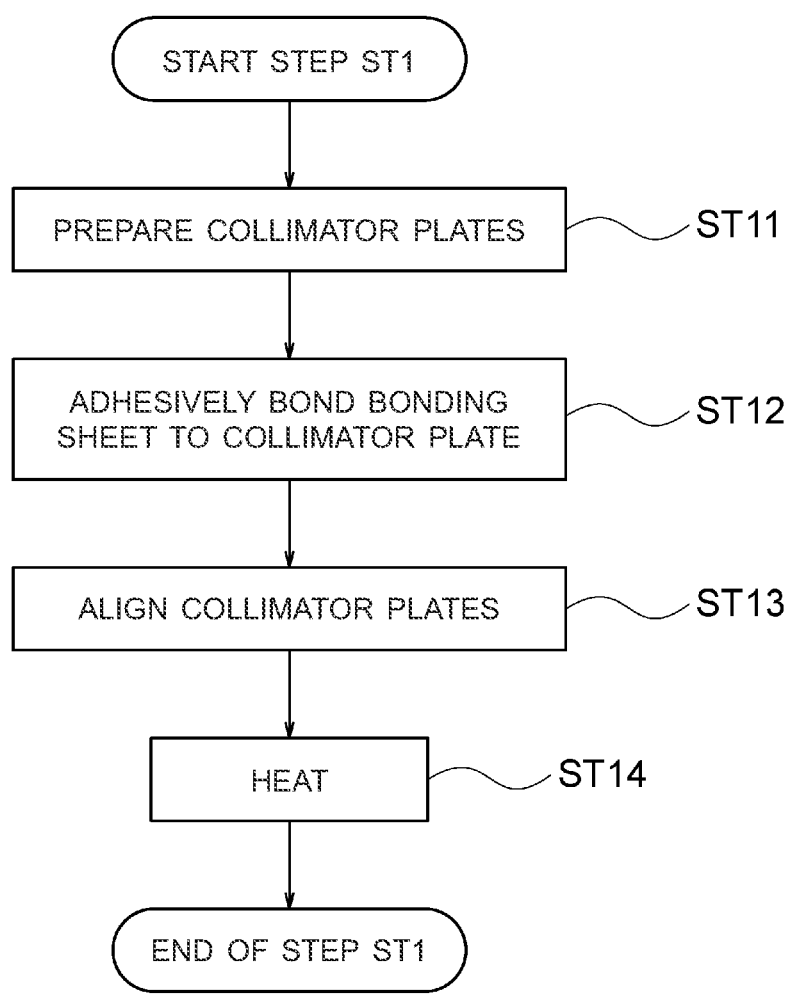
FIG. 17 is a flow chart of an example of a method of making the collimator plate set 2.

FIG. 17 is a flow chart of the example of the method of making the collimator plate set 2.

At Step ST11, the collimator plates 3 and 4 are prepared (see FIGS. 14 and 15).

Figure 18:
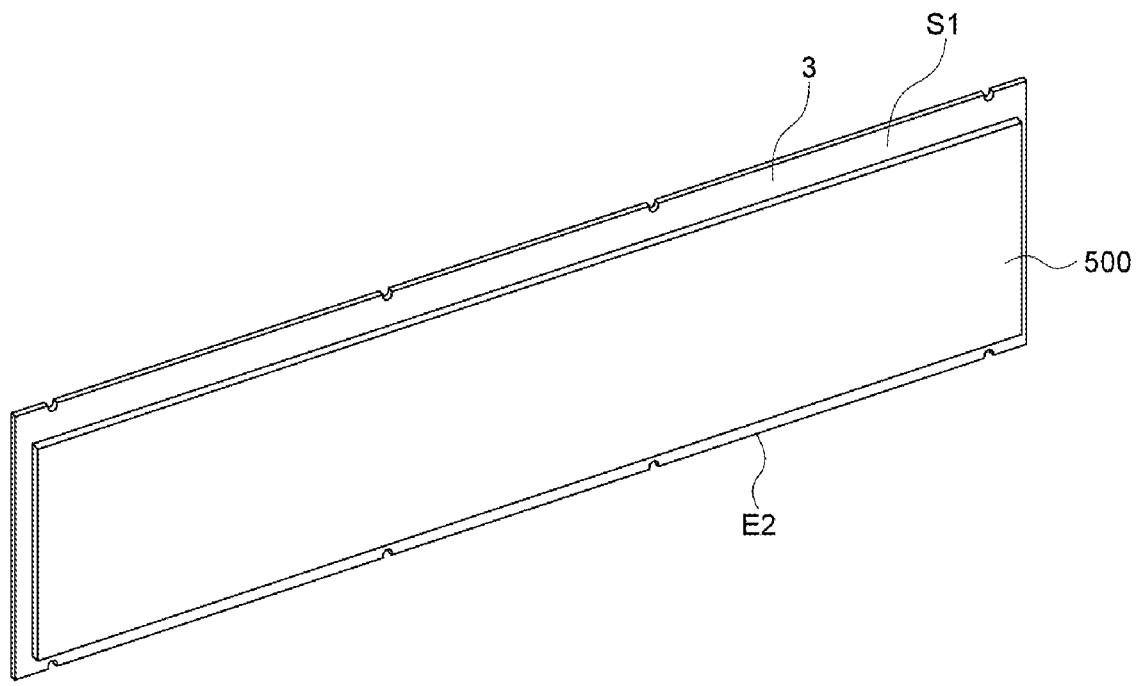
FIG. 18 is a perspective view showing the collimator plate 3, and a bonding sheet 500 adhesively bonded to the collimator plate 3.

At Step ST12, a bonding sheet 500 is adhesively bonded to the first surface 51 of the collimator plate 3 (see FIGS. 18 and 19).

FIG. 18 is a perspective view showing the collimator plate 3 and the bonding sheet 500 adhesively bonded to the collimator plate 3, and FIG. 19 is a side view and a bottom plan view of the collimator plate 3 and bonding sheet 500 shown in FIG. 18.

For the bonding sheet 500, an epoxy-resin bonding sheet having an adhesive layer may be used, for example. For such an epoxy-resin bonding sheet, for example, a sheet in which a thermally foaming filler is added to the adhesive layer, and which is designed to have an expanded volume by foaming under heating, may be used. Although the present embodiment addresses an example in which such a sheet designed to have an expanded volume by heating described above is used as the bonding sheet 500, the invention is not limited to the sheet, and various sheets capable of joining the collimator plates 3 and 4 together may be used. After adhesively bonding the bonding sheet 500 to the collimator plate 3, the flow goes to Step ST13.

Figure 20:
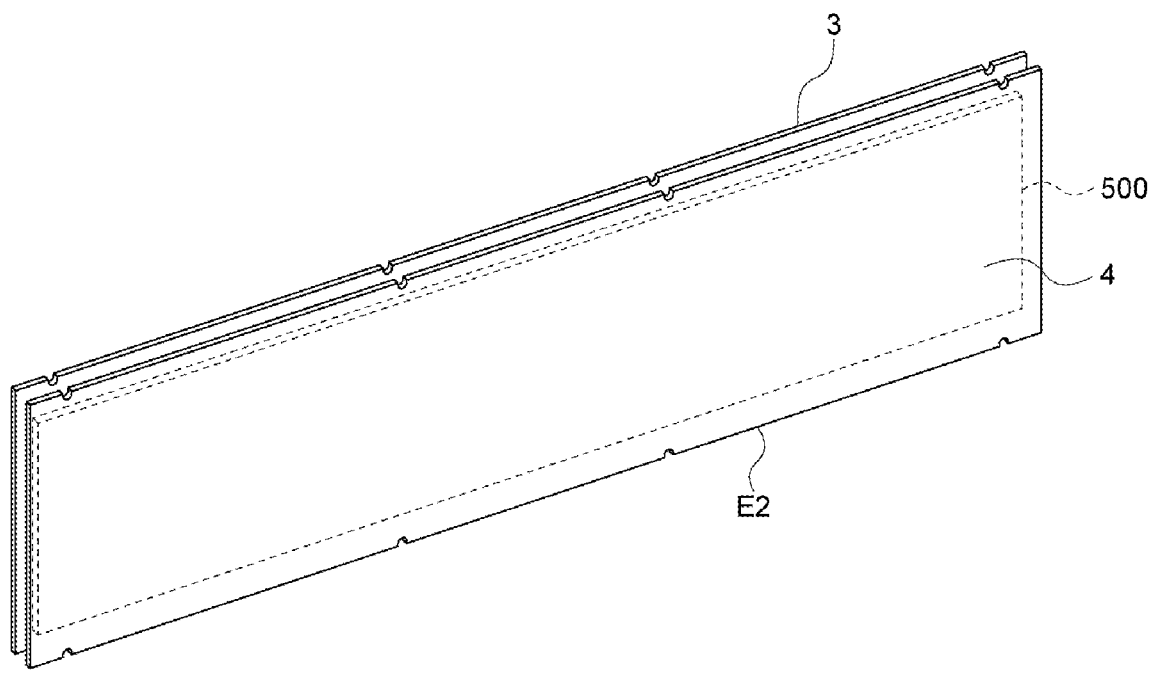
FIG. 20 is a perspective view of the collimator plates 3 to which the bonding sheet 500 is adhesively bonded, and the collimator plate 4 aligned to the collimator plate 3.
Figure 21:
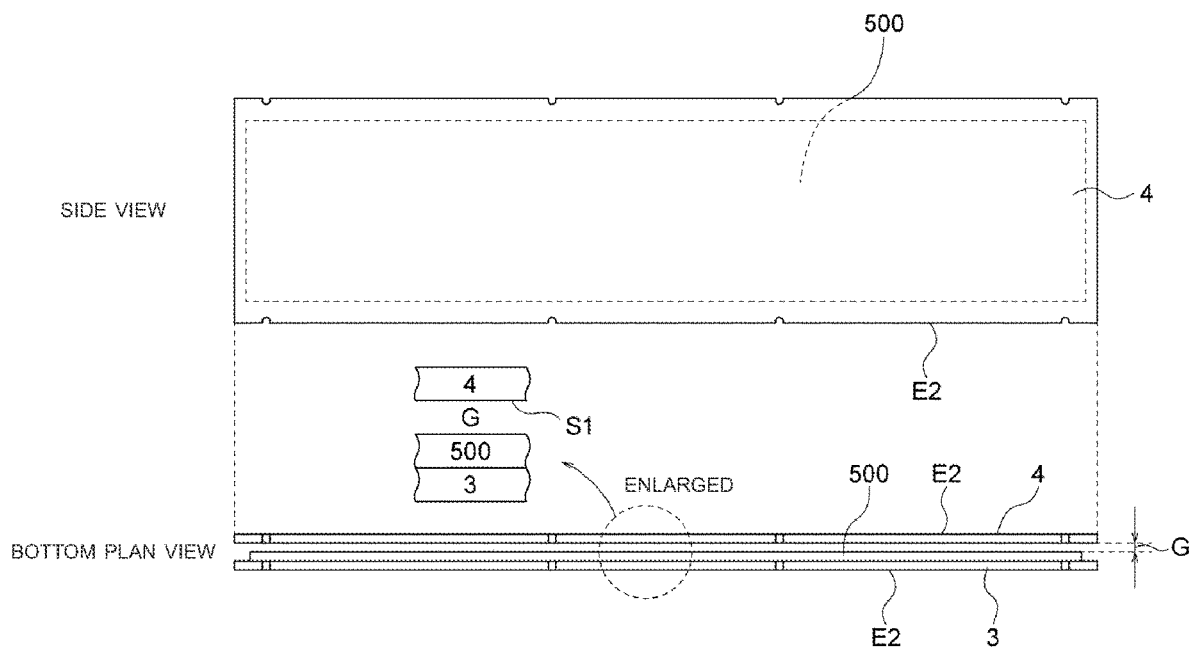
FIG. 21 is a side view and a bottom plan view of the collimator plates, etc. shown in FIG. 20.

At Step ST13, the collimator plate 4 is aligned to the collimator plate 3 to which the bonding sheet 500 has been adhesively bonded (see FIGS. 20 and 21).

FIG. 20 is a perspective view showing the collimator plate 3 to which the bonding sheet 500 is adhesively bonded, and the collimator plate 4 aligned to the collimator plate 3, and FIG. 21 is a side view and a bottom plan view of the collimator plates, etc. shown in FIG. 20.

At Step ST13, the collimator plate 4 is aligned to the collimator plate 3 so that a predetermined gap G is retained between the first surface S1 of the collimator plate 4 and the bonding sheet 500, with the first surface S1 of the collimator plate 4 facing the bonding sheet 500. The collimator plate 4 may be aligned to the collimator plate 3 by using an alignment jig, which is not shown.

The value of the gap G between the collimator plate 4 and bonding sheet 500 is set taking account of how much the bonding sheet 500 will expand by heating processing at Step ST14, which will be discussed later. The gap G may be set to, for example, several hundreds of micrometers. After aligning the collimator plate 4, the flow goes to Step ST14.

Figure 22:
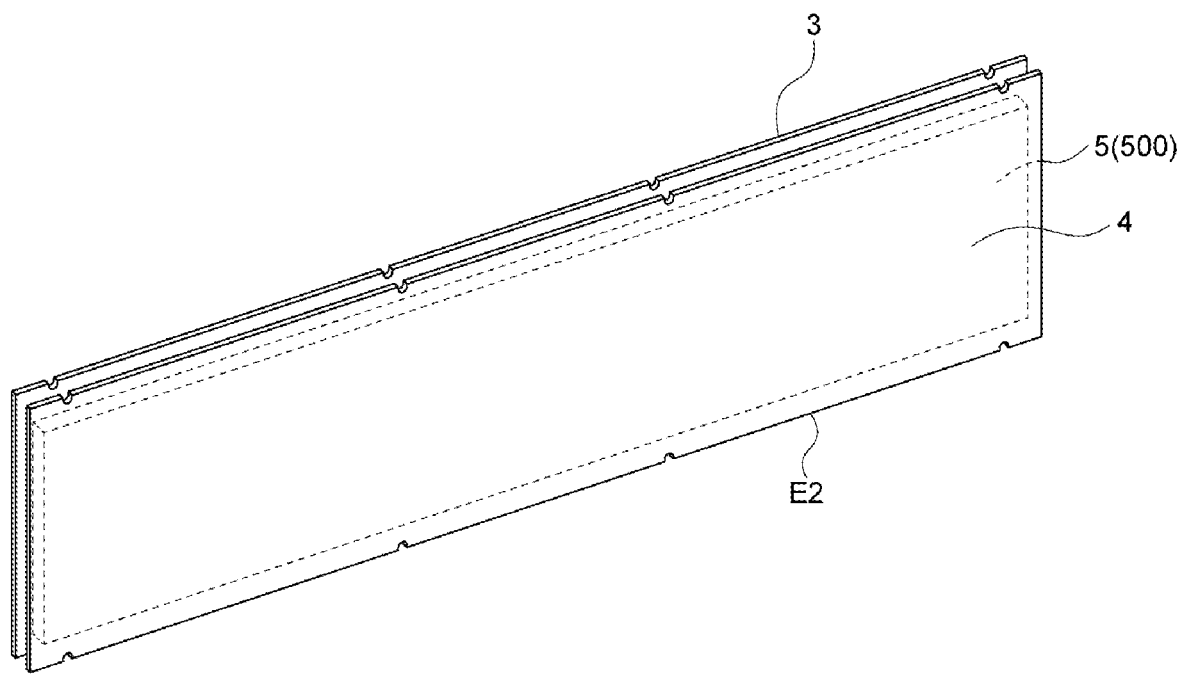
FIG. 22 is a perspective view showing the collimator plates 3 and 4 after heating the bonding sheet 500.
Figure 23:
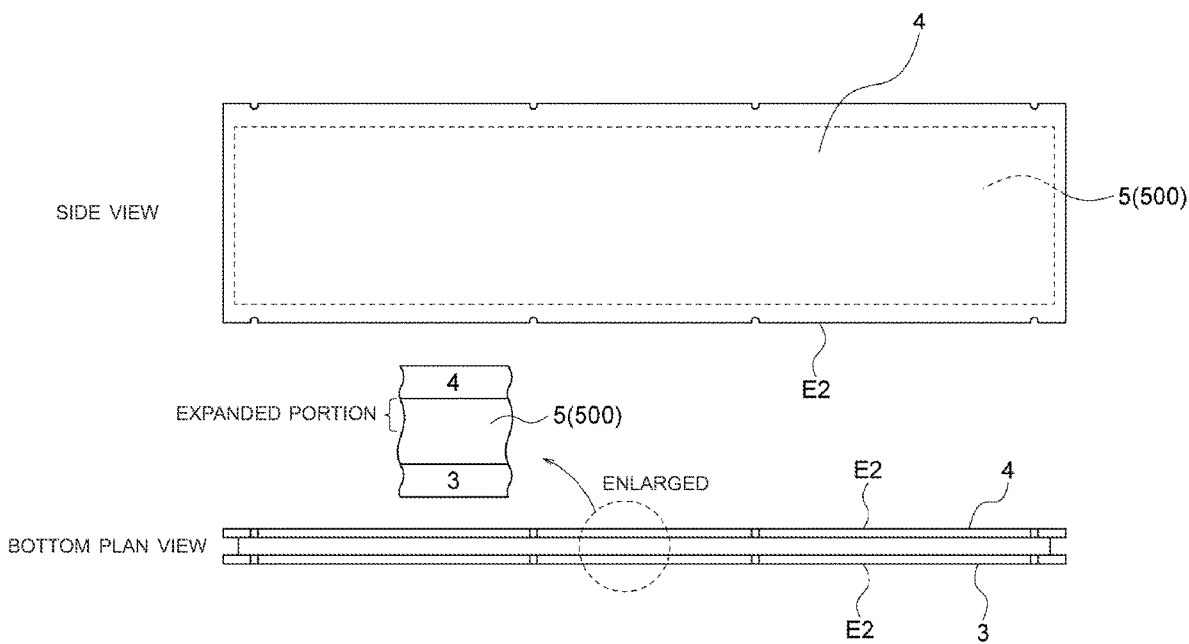
FIG. 23 is a side view and a bottom plan view of the collimator plates, etc. shown in FIG. 22.

At Step ST14, the bonding sheet 500 is heated. FIG. 22 is a perspective view showing the collimator plates 3 and 4 after heating of the bonding sheet 500, and FIG. 23 is a side view and a bottom plan view of the collimator plates, etc. shown in FIG. 22.

Heating of the bonding sheet 500 causes the bonding sheet 500 to expand to fill the gap G, and to be adhesively bonded to the collimator plate 4. The collimator plates 3 and 4 can thus be joined together.

In this way, the flow in FIG. 17 is completed, and the collimator plate set 2 can thus be made. It should be noted that the sheet 500 after expansion turns into the joint layer 5 for joining the collimator plates 3 and 4 together.

Returning to FIG. 16, the description will be continued.

After the collimator plate sets 2 in a number required to make a collimator module 1 have been prepared, the flow goes to Step ST2.

Figure 24:
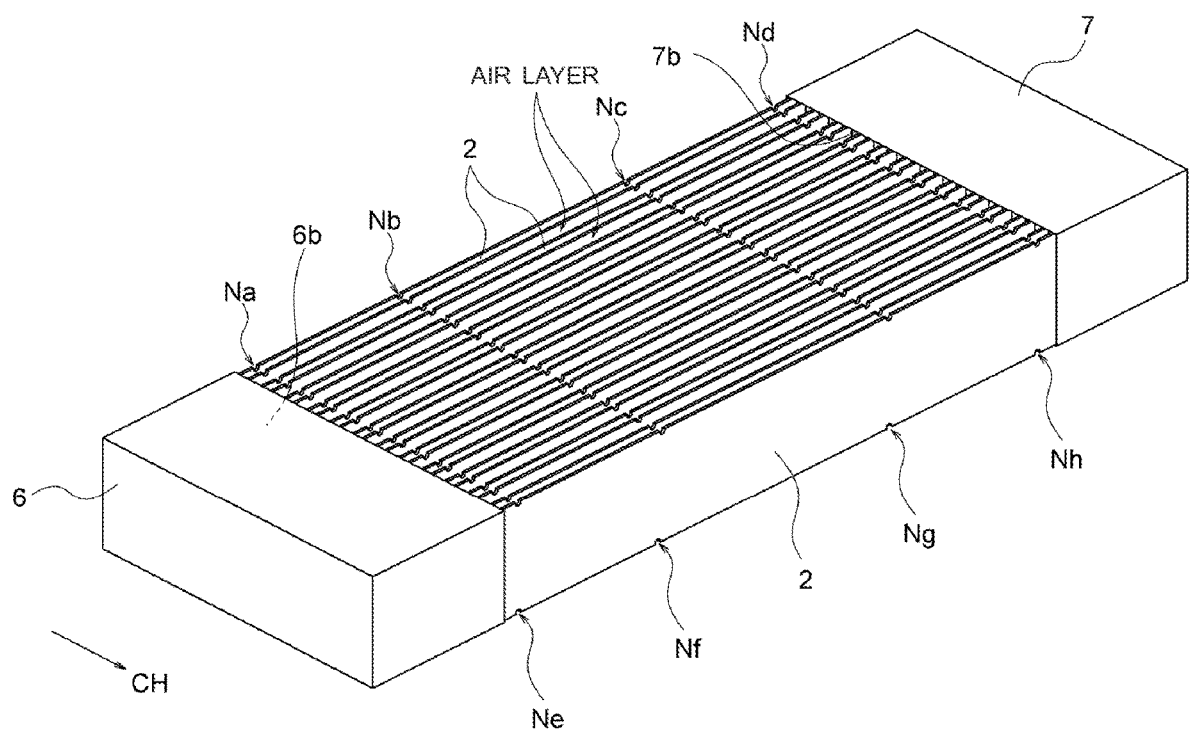
FIG. 24 is a view showing a plurality of collimator plate sets 2 inserted into slots 6b and 7b in brackets 6 and 7.

At Step ST2, the plurality of collimator plate sets 2 are inserted into the slots 6b and 7b in the brackets 6 and 7 (see FIG. 10). FIG. 24 schematically shows the brackets 6 and 7, and the plurality of collimator plate sets 2 inserted into the slots 6b and 7b in the brackets 6 and 7. By inserting the plurality of collimator plate sets 2 into the slots 6b and 7b in the brackets 6 and 7, an air layer can be made to intervene between the adjacent collimator plate sets 2.

Next, the flow goes to Step ST3.

At Step ST3, registration of the collimator plate sets 2 is performed. The registration is performed to register the collimator plate sets 2 in the channel direction CH with good precision. For the registration, a jig for making a collimator module disclosed in the gazette of Japanese Patent Application KOKAI No. 2015-108587 (e.g., in Paragraphs [0052]-[0066]) may be used. After performing the registration of the collimator plate sets 2, the flow goes to Step ST4.

Figure 25:
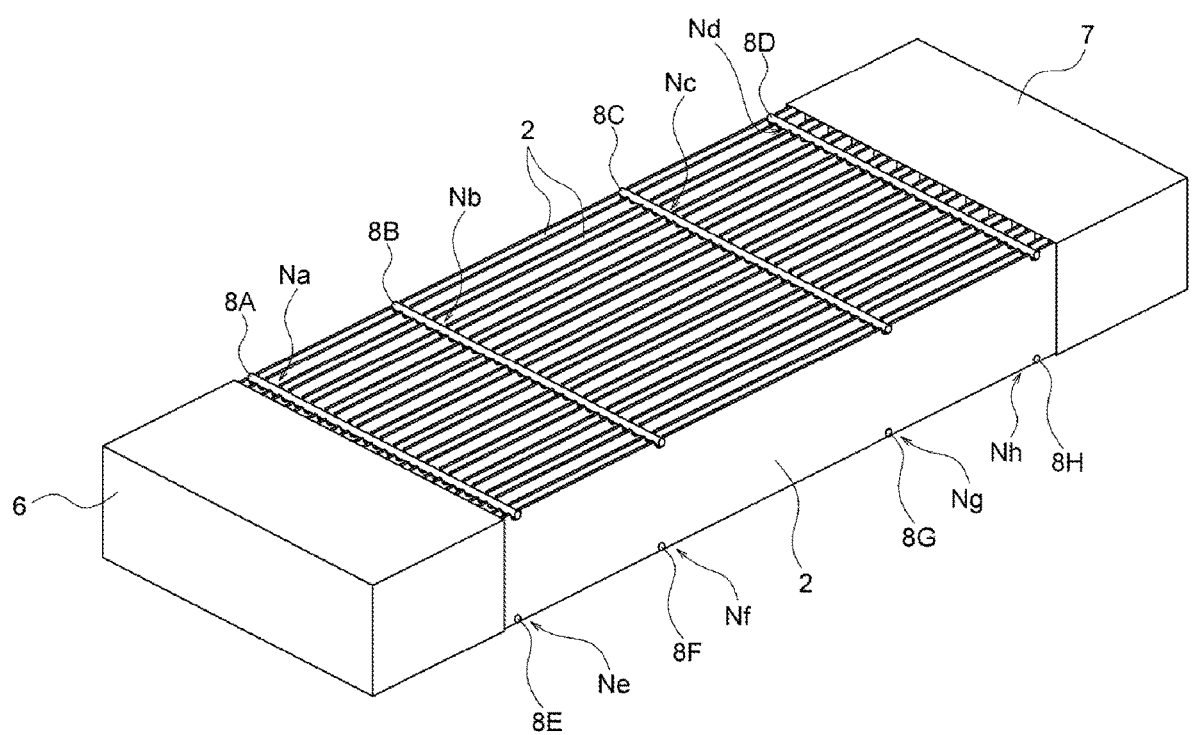
FIG. 25 is a view in which fixing rods are inserted into notches.

At Step ST4, the upper fixing rods 8A to 8D are inserted into the notches Na to Nd (see FIG. 25), and the upper fixing rods 8A to 8D and the collimator plate sets 2 are adhesively bonded together by an adhesive. Likewise, the lower fixing rods 8E to 8H are inserted into the notches Ne to Nh, and the lower fixing rods 8E to 8H and the collimator plate sets 2 are adhesively bonded together by an adhesive. Furthermore, the collimator plate sets 2 and brackets 6 and 7 are adhesively bonded together.

Next, the flow goes to Step ST5.

At Step ST5, an upper side of the collimator plate sets 2 is adhesively bonded with the upper reinforcing plate 9, and a lower side of the collimator plate sets 2 is adhesively bonded with the lower reinforcing plate 10.

In this way, the collimator module 1 can be made.

As described above, in the collimator module 1 in the present embodiment, the collimator plates 3 and 4 are joined together by the joint layer 5. Therefore, when intervals between the detector elements are reduced in accordance with a finer resolution (a reduced size of each detector element), an effect that the collimator plates 3 and 4 can be made resistant to deformation while keeping X-ray use efficiency can be achieved. Now a reason why this effect is achieved will be described hereinbelow in comparison with a collimator module having no joint layers 5.

FIG. 26 is an explanatory diagram for the effect of the collimator module 1 having the joint layers 5.

Figure 1:
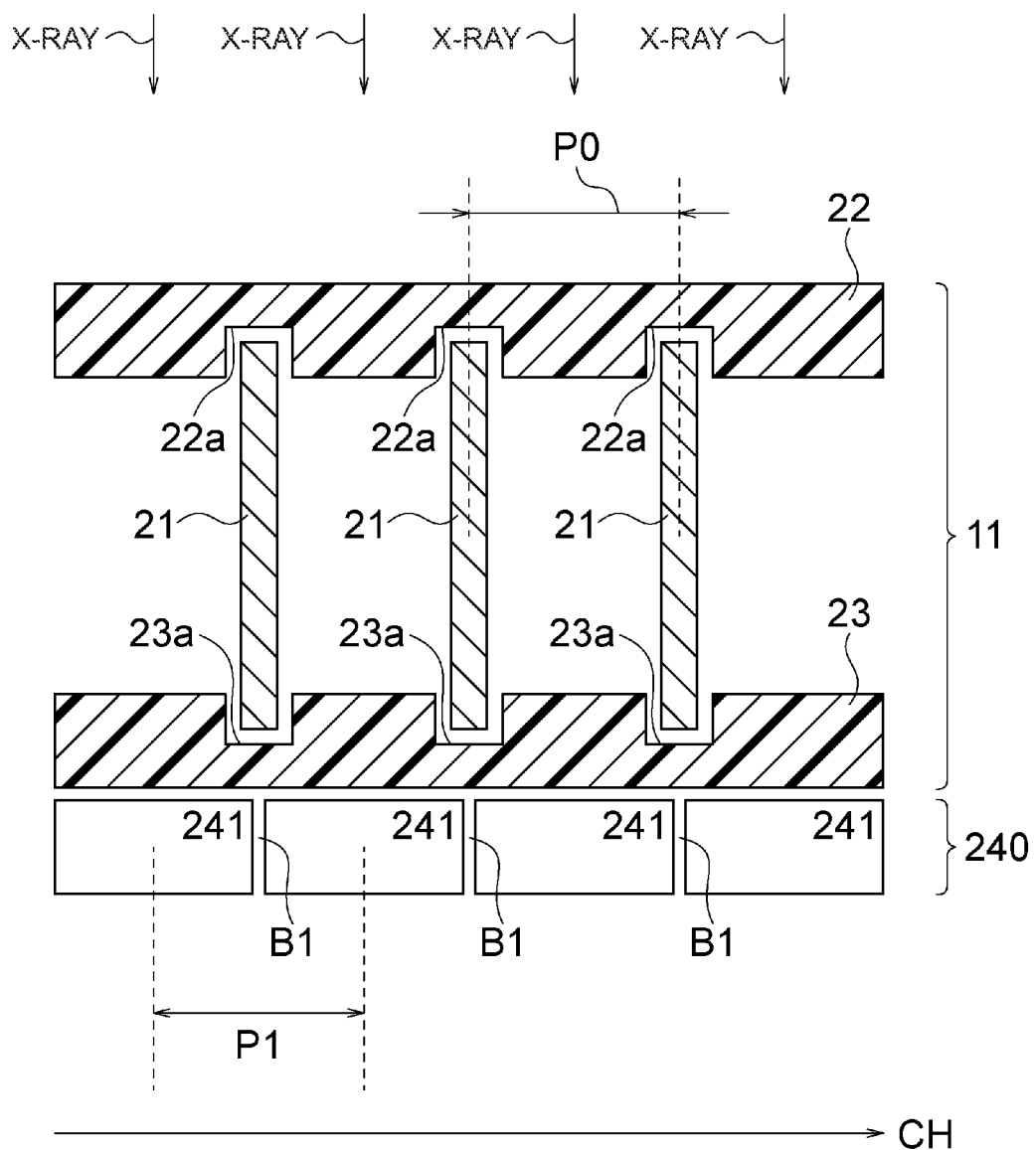
FIG. 1 is a schematic cross-sectional view of part of a collimator module 11.
Figure 2:
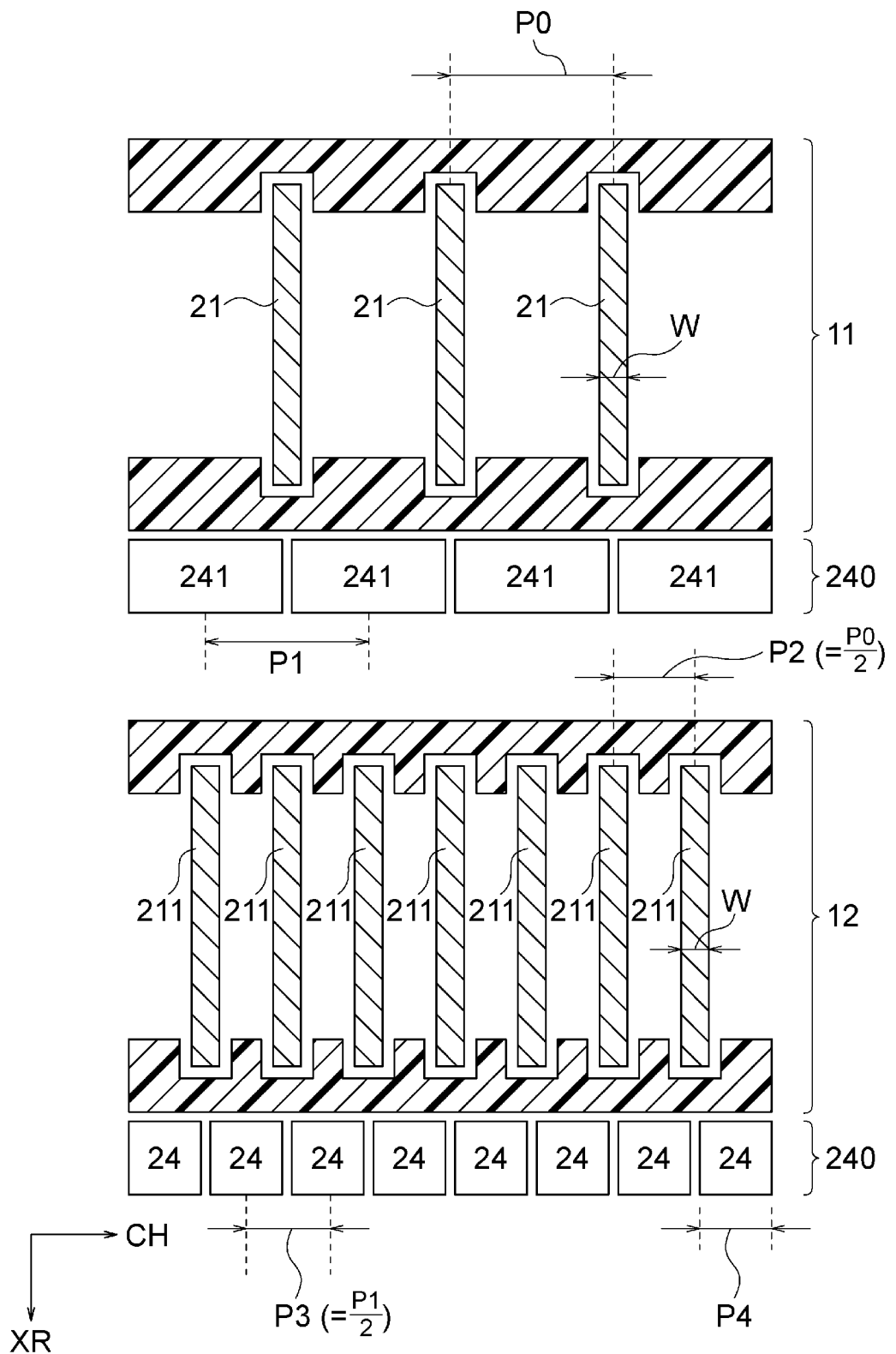
FIG. 2 is a diagram showing a collimator module in which detector element-to-element intervals are each approximately halved.
Figure 3:
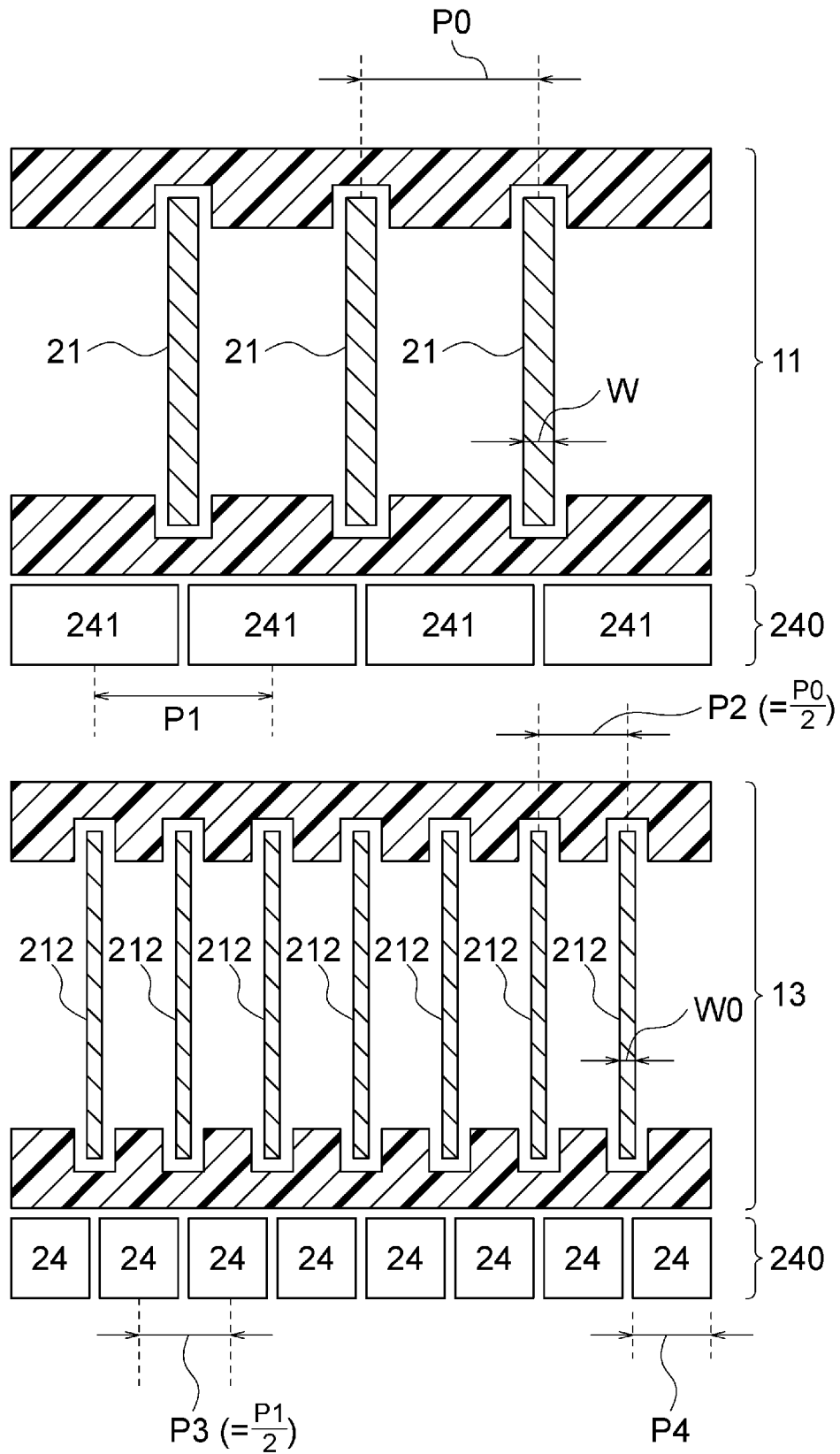
FIG. 3 is a diagram showing an example in which the thickness of the collimator plate is reduced.

The collimator module 1 having the joint layers 5 in the present embodiment is shown in the lower portion of FIG. 26. FIG. 26 also shows in its upper portion the collimator module 13 having no joint layers 5 as a comparative example. The collimator module 13 shown in the upper portion of FIG. 26 is that shown in FIG. 3 described earlier.

First, the collimator module 13 having no joint layers 5 in the comparative example will be briefly described. As described earlier referring to FIG. 3, the collimator plates 212 having a smaller plate thickness are employed in the collimator module 13 in the comparative example in order to enhance X-ray use efficiency. Therefore, the collimator plates 212 have lowered rigidity, posing a problem that the collimator plates 212 are vulnerable to deformation.

On the other hand, the collimator module 1 in the present embodiment comprises the collimator plate sets 2 in each of which the two collimator plates 3 and 4 are joined together by the joint layer 5. The collimator plates 3 and 4 have a thickness w0 that is the same as the collimator plates 212. However, since in the collimator plate set 2, the joint layer 5 joins the collimator plates 3 and 4 together, the joint layer 5 and collimator plates 3 and 4 can synergically provide the collimator plate set 2 having enhanced rigidity as a whole. Therefore, the collimator plates 3 and 4 used in the collimator module 1 in the present embodiment are capable of enhancing rigidity of the collimator plates 3 and 4 in spite of the fact that they have the same thickness as the collimator plates 212 used the collimator module 13 in the comparative example, so that the collimator plates 3 and 4 can be made resistant to deformation while restraining lowering of X-ray use efficiency.

Moreover, the collimator module 1 in the present embodiment has the air layer 20 intervening between two adjacent collimator plate sets 2, in place of the joint layer 5. By the intervening air layers 20, there is provided an effect that position offset in the collimator plates 3 and 4 in the channel direction CH can be reduced under thermal expansion of the joint layer 5. Now a reason why this effect is achieved will be described hereinbelow. In describing this effect, a collimator module having no intervening air layers 20 will be first described to clarify a problem of the collimator module having no intervening air layers 20. After clarifying the problem, the effect of the intervening air layers 20 will be then described.

Figure 27:
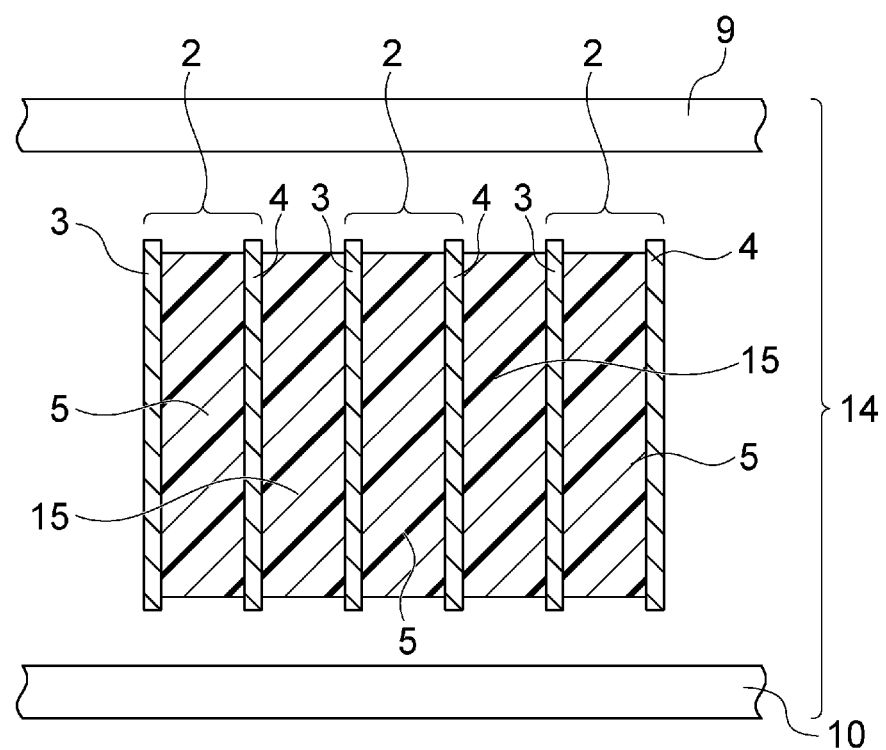
FIG. 27 is a cross-sectional view of a collimator module 14 having no intervening air layers 20.

FIG. 27 is a cross-sectional view of a collimator module 14 having no intervening air layers 20.

The collimator module 14 in FIG. 27 has a joint layer 15 filled between two adjacent collimator plate sets 2, in place of the air layer 20. Therefore, in the collimator module 14 in FIG. 27, the adjacent collimator plate sets 2 are joined together by the joint layer 15.

Figure 28:
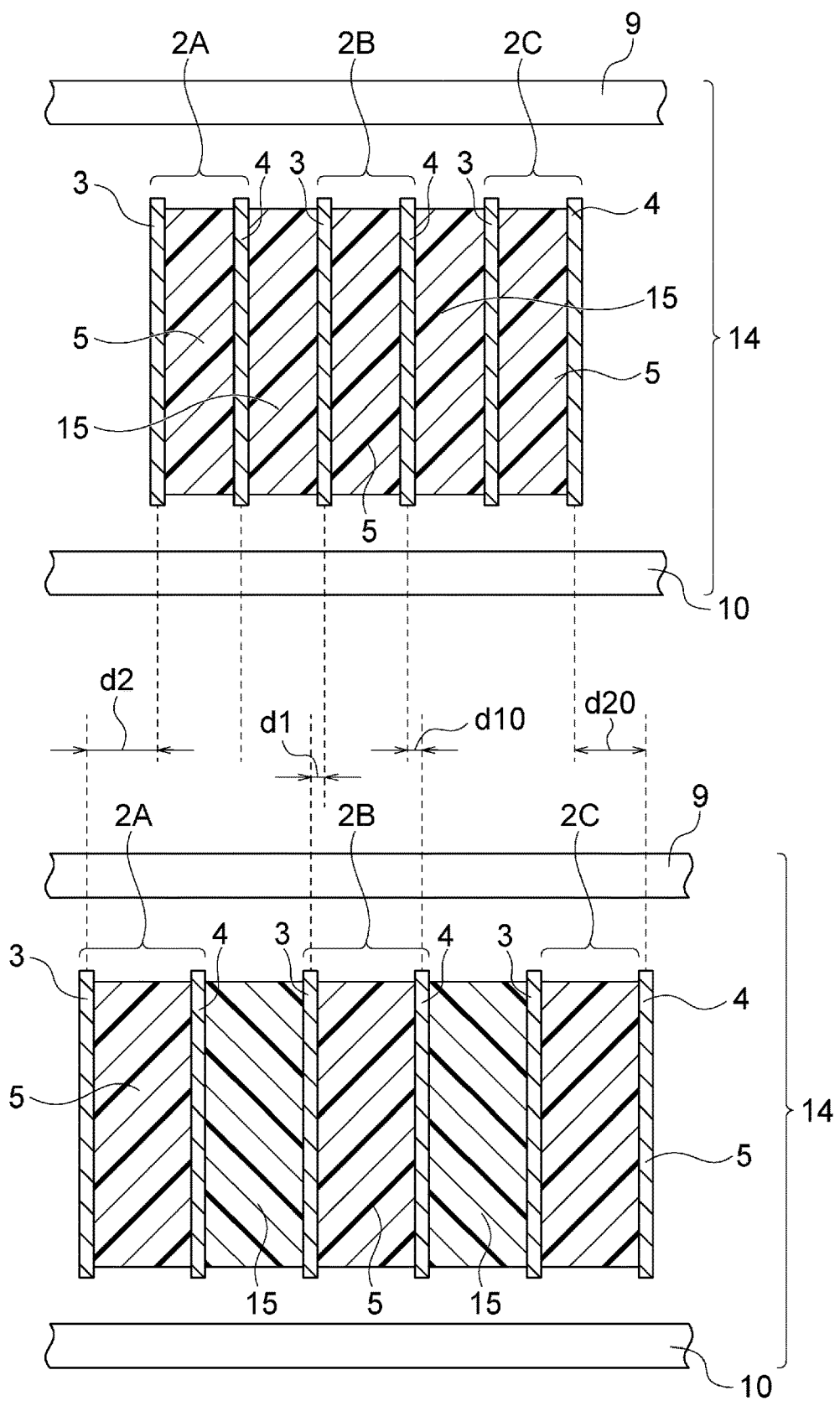
FIG. 28 is an explanatory diagram for a problem of the collimator module 14 shown in FIG. 27.

FIG. 28 is an explanatory diagram for a problem of the collimator module 14 shown in FIG. 27.

FIG. 28 shows in its upper portion a cross-sectional view of the collimator module 14 before the joint layers 5 and 15 thermally expand, and in its lower portion a cross-sectional view of the collimator module 14 after the joint layers 5 and 15 have thermally expanded.

In FIG. 28, to distinguish among the collimator plate sets 2, they are designated by Symbols "2A," "2B," and "2C," in place of Symbol "2."

The joint layers 5 and 15 in the collimator module 14 thermally expand depending upon the surrounding temperature environment. Therefore, considering the collimator plate set 2B, the collimator plate 3 in the collimator plate set 2B exhibits a position offset of d1 due to thermal expansion of the joint layer 5.

Next, consider the collimator plate set 2A. The collimator plate set 2A lies next to the collimator plate set 2B via the joint layer 15. Therefore, thermal expansion of the joint layer 5 in the collimator plate set 2B induces a position offset of the collimator plate 3 in the collimator plate set 2A via the joint layer 15. Thus, the collimator plate 3 in the collimator plate set 2A exhibits a position offset due to thermal expansion of the joint layer 5 in the collimator plate set 2A, and in addition, that of the joint layer 5 in the collimator plate set 2B. Consequently, a position offset d2 of the collimator plate 3 in the collimator plate set 2A is larger than the position offset d1 of the collimator plate 3 in the collimator plate set 2B.

For a similar reason, the collimator plate 4 in the collimator plate set 2C has a position offset d20 larger than the position offset d10 of the collimator plate 4 of the collimator plate set 2B.

Therefore, by providing the joint layer 15 between the collimator plate sets 2, thermal expansion of the joint layer 5 in a collimator plate set 2 induces a position offset of a next collimator plate set 2 via the joint layer 15. The position offset of the collimator plate 3 (or 4) thus accumulates in the channel direction CH, disadvantageously resulting in an increased position offset of the collimator plate 3 (or 4) in the channel direction CH.

Accordingly, to restrain such a phenomenon that the position offsets of the collimator plates 3 and 4 increase, the collimator module 1 in the present embodiment has the air layer 20 (see FIG. 26) intervening between the adjacent collimator plate sets 2.

By the air layer 20 intervening between the collimator plate sets 2, when the joint layer 5 in the collimator plate set 2 thermally expands, the thermally expanding joint layer 5 can be prevented from inducing position offsets of the collimator plates in the next collimator plate set 2. Therefore, a risk of accumulation of the position offset in the collimator plate sets 3 and 4 in the channel direction CH can be reduced, so that the position offsets of the collimator plates 3 and 4 in the channel direction CH can be reduced. Moreover, since the position offsets of the collimator plates 3 and 4 in the channel direction CH can be reduced, it is possible to reduce non-uniformity in detection by the X-ray detector 542 in the channel direction.

Figure 29:
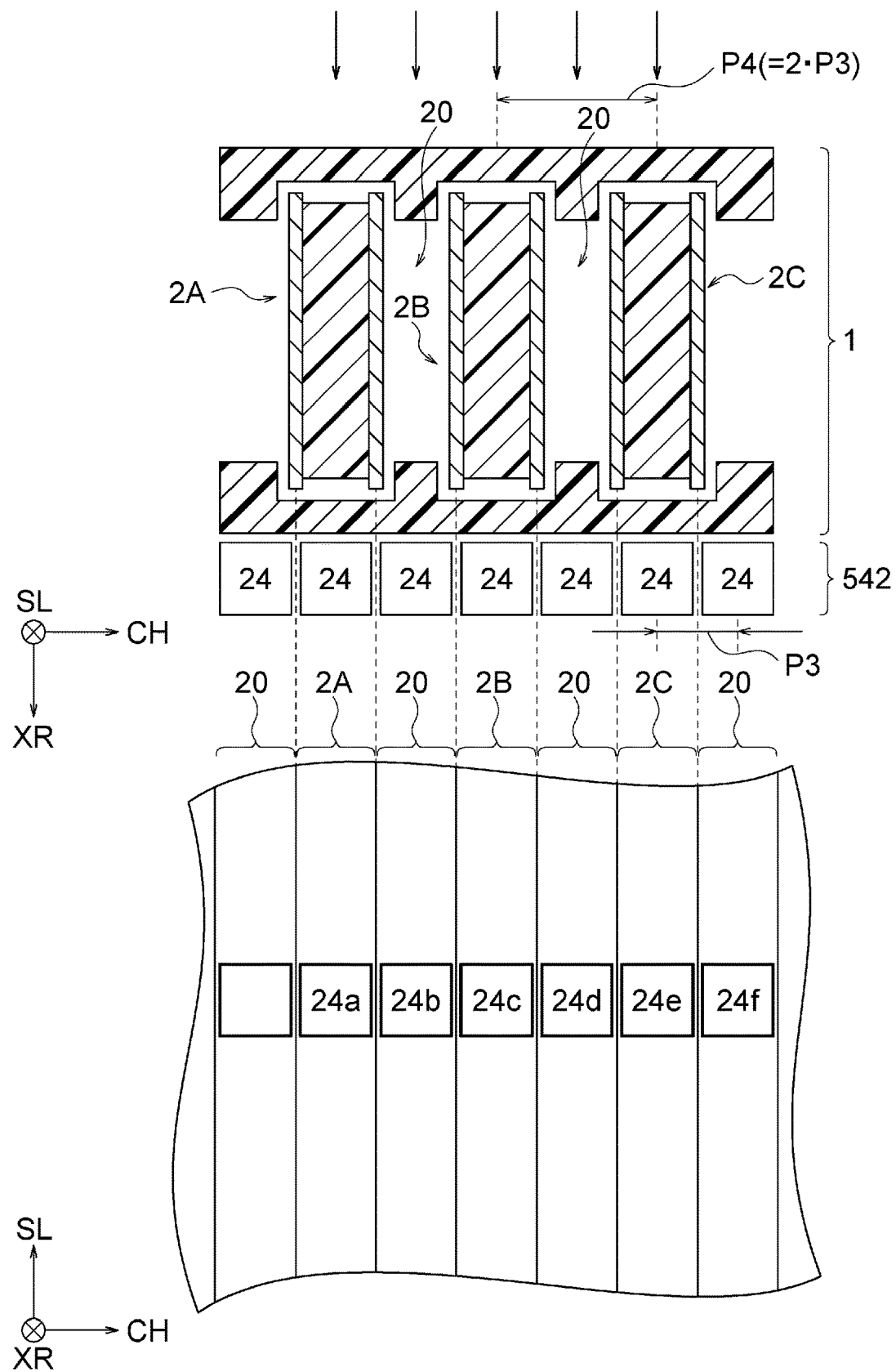
FIG. 29 is a diagram schematically showing a positional relationship between the collimator plate sets 2 and detector elements 24.

Next, a positional relationship between the collimator plate sets 2 in the collimator module 1 and detector elements that the X-ray detector 542 (see FIG. 6) has, will be studied (see FIG. 29).

FIG. 29 is a diagram schematically showing the positional relationship between the collimator plate sets 2 in the detector module 1 and detector elements 24 the X-ray detector 542 (see FIG. 6) has.

FIG. 29 shows in its upper portion a cross-sectional view of the collimator plate sets 2 and detector elements 24 as viewed in the slice direction SL, and in its in lower portion a top plan view thereof as viewed in a direction XR of X-ray emission.

Note that in the top plan view, the reinforcing plates are omitted in the drawing so as to clarify the positional relationship between the collimator plate sets 2 and detector elements 24, and the collimator plate sets 2 are shown in thin lines while the detector elements 24 are shown in bold lines. Although the detector elements 24 are actually two-dimensionally arranged, only those lined up on a specific line in the channel direction CH are shown here for convenience of explanation. Moreover, to distinguish among the collimator plate sets 2, they are designated by Symbols "2A," "2B," and "2C," in place of Symbol "2." Furthermore, to distinguish among the detector elements 24 lined up in the channel direction CH, they are designated by Symbols "24a," "24b," "24c," "24d," "24e," and "24f," in place of Symbol "24."

The detector elements 24 (24a to 24f) line up in the channel direction CH at intervals of P3. On the other hand, the collimator plate sets 2A, 2B, and 2C are aligned to line up side by side in the channel direction CH at intervals of P4. The interval P4 is set to fulfill a condition that it is twice the interval P3, that is, P4=2*P3.

While the detector elements 24a, 24c, and 24e underlie the collimator plate sets 2A, 2B, and 2C, respectively, in viewing the collimator module 1 in the direction XR of X-ray emission, the next detector elements 24b, 24d, and 24f underlie the air layers 20. Therefore, considering the detector elements 24a to 24f lined up in the channel direction CH in FIG. 29, there appear detector elements underlying the collimator plate sets 2A, 2B, or 2C, and those underlying the air layer 20 in an alternating manner. In the case that the joint layers 5 of the collimator plate sets 2A, 2B, and 2C have an X-ray absorption property adequately close to that of the air layer 20, the amount of X-rays reaching the detector elements 24a to 24f may be considered to be substantially the same among them. However, in the case that the joint layers 5 have an X-ray absorption property quite different from that of the air layer 20, this poses a problem that variabilities in the amount of X-rays detected at the detector elements 24a to 24f becomes higher. Accordingly, a method for addressing this problem will now be described hereinbelow referring to FIG. 30.

Figure 30:
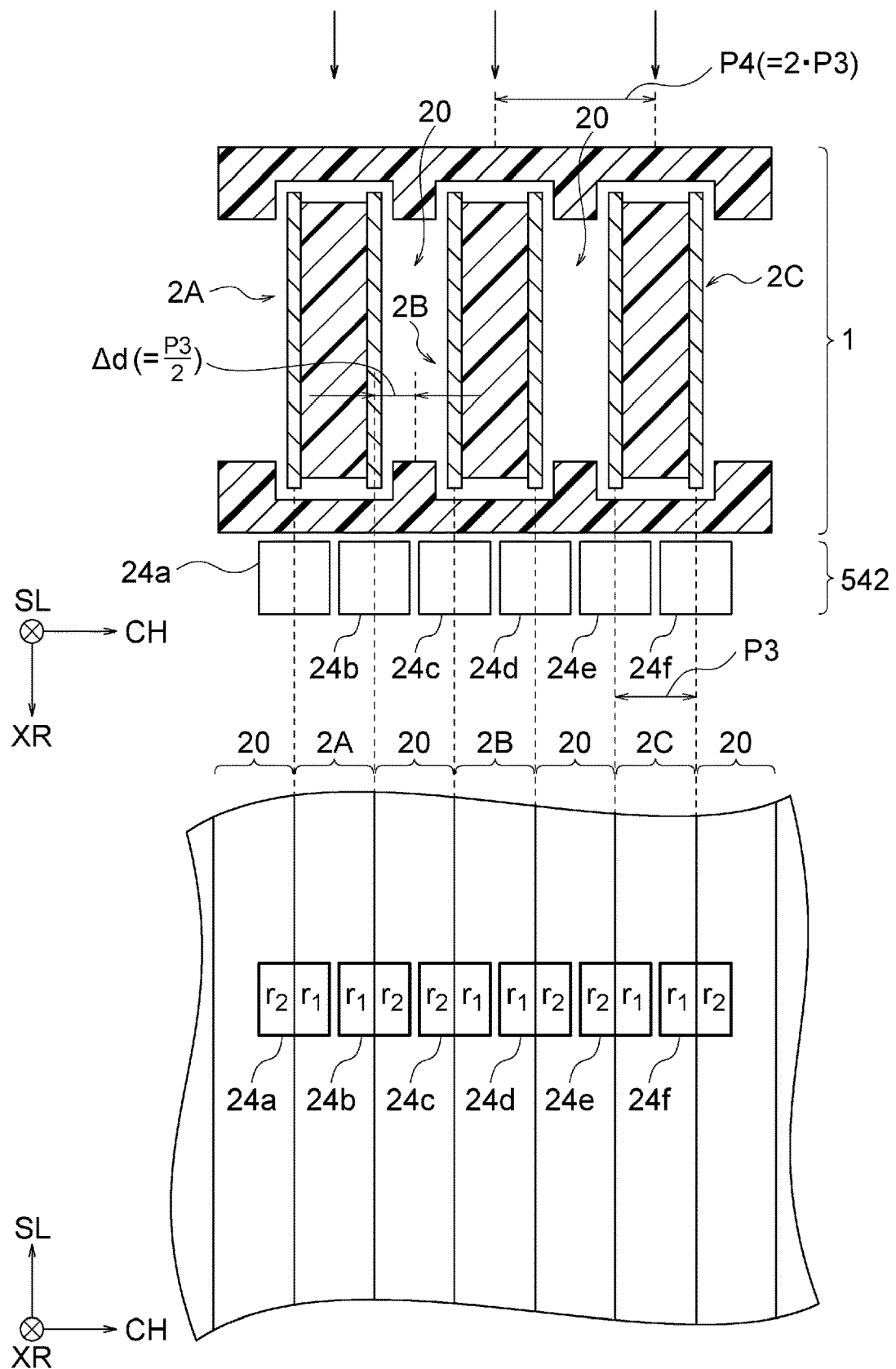
FIG. 30 is an explanatory diagram for an example of a method of reducing variabilities in the amount of X-rays detected at the detector elements 24.

FIG. 30 is an explanatory diagram for an example of a method of reducing variabilities in the amount of X-rays detected at the detector elements 24.

As compared with the collimator module 1 in FIG. 29, the collimator module 1 in FIG. 30 is different in that the collimator plate sets 2 (2A to 2C) are aligned to the detector elements 24 (24a to 24f) in the X-ray detector 542 with an offset of Δd (a half of the interval P3 for the detector elements) in the channel direction CH.

Therefore, when viewing in the direction XR of X-ray emission, the collimator plate sets 2A, 2B, and 2C each partially overlap two detector elements adjoining in the channel direction CH, rather than overlying a single detector element.

Figure 31:
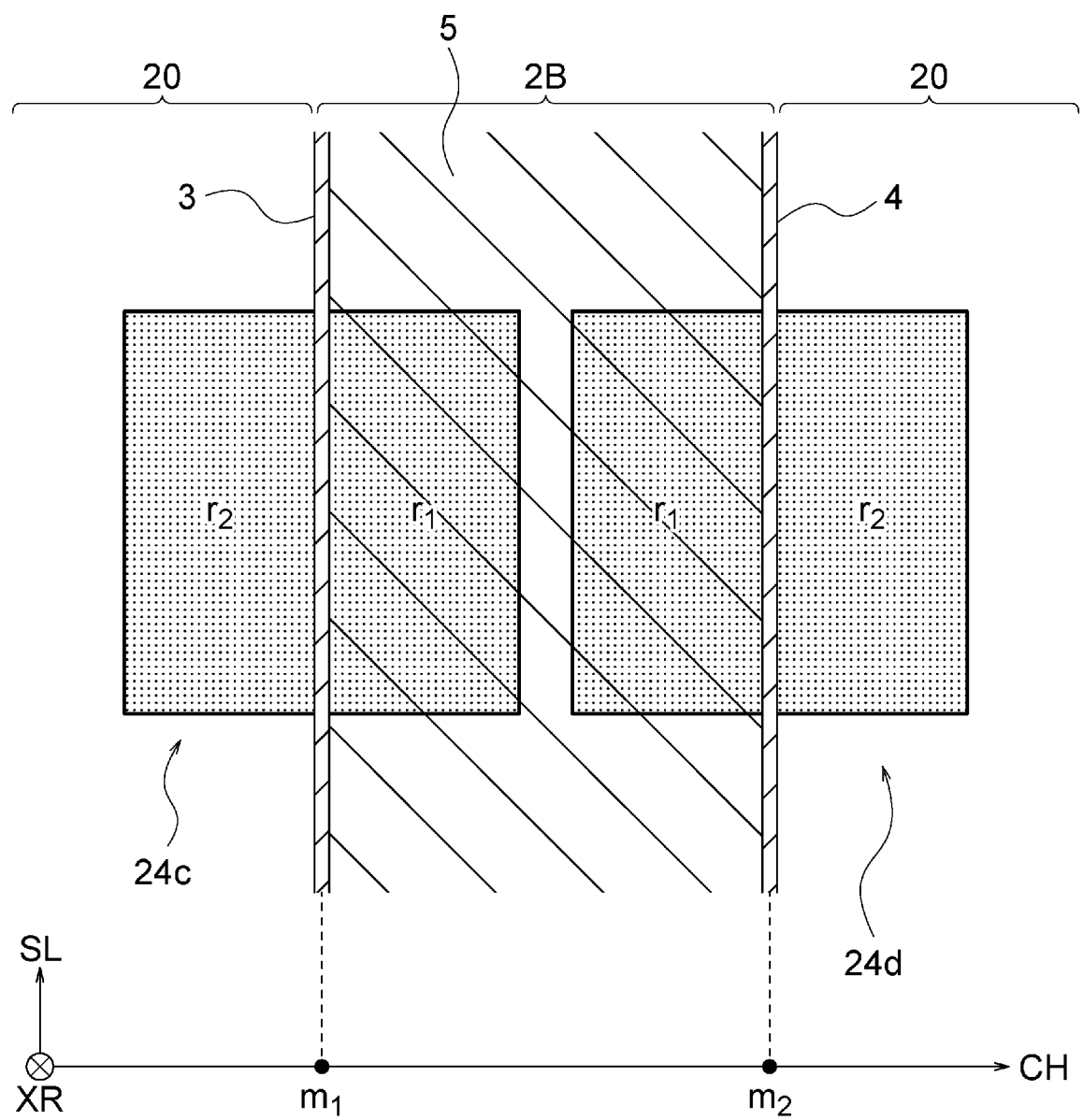
FIG. 31 is an enlarged view of a collimator plate set 2B and detector elements 24c and 24d as viewed in a direction XR of X-ray emission.

For example, considering the collimator plate set 2B, it partially overlaps each of two detector elements 24c and 24d adjoining in the channel direction CH. FIG. 31 is an enlarged view of the collimator plate set 2B and detector elements 24c and 24d as viewed in the direction XR of X-ray emission.

As shown in FIG. 31, when viewing in the direction XR of X-ray emission, the one collimator plate 3 in the collimator plate set 2B is aligned to divide one detector element 24c of the two adjoining detector elements 24c and 24d into two portions in the channel direction CH. Specifically, when viewing in the direction XR of X-ray emission, the collimator plate 3 is aligned to intersect a center position m1 of the detector element 24c in the channel direction CH. On the other hand, when viewing in the direction XR of X-ray emission, the other collimator plate 4 in the collimator plate set 2B is aligned to divide the other detector element 24d into two portions in the channel direction CH. Specifically, when viewing in the direction XR of X-ray emission, the collimator plate 4 is aligned to intersect a center position m2 of the detector element 24d in the channel direction CH. Therefore, when viewing in the direction XR of X-ray emission, the detector element 24c includes a region r1 underlying the joint layer 5 of the collimator plate set 2B, and a region r2 underlying the air layer 20. Likewise, when viewing in the direction XR of X-ray emission, the detector element 24d next to the detector element 24c includes a region r1 underlying the joint layer 5 of the collimator plate set 2B, and a region r2 underlying the air layer 20.

Next, returning to FIG. 30, let us consider the collimator plate set 2A adjacent to the collimator plate set 2B. The collimator plate set 2A partially overlaps each of the two detector elements 24a and 24b adjoining in the channel direction CH. Therefore, when viewing in the direction XR of X-ray emission, the detector element 24a includes a region r1 underlying the joint layer 5 of the collimator plate set 2A, and a region r2 underlying the air layer 20. Likewise, when viewing in the direction XR of X-ray emission, the detector element 24b next to the detector element 24a includes a region r1 underlying the joint layer 5 of the collimator plate set 2A, and a region r2 underlying the air layer 20.

Therefore, when viewing in the direction XR of X-ray emission, the plurality of collimator plate sets 2A to 2C are aligned to the X-ray detector 542 so that the detector elements 24a to 24f each have a first region r1 underlying the joint layer 5 and a second region r2 underlying the air layer 20.

By such a configuration, each detector element 24 can be configured so that an approximately half region r1 underlies the joint layer 5 and the remaining approximately half region r2 underlies the air layer 20, with respect to the direction XR of X-ray emission.

Therefore, since every detector element 24 detects both X-rays having passed through the joint layer 5 and those having passed through the air layer 20, variabilities in the detected amount of X-rays among the detector elements 24 can be reduced, and non-uniformity in detection of the amount of X-rays in the channel direction can be reduced as well.

It should be noted that in FIGS. 29 and 30, when viewing in the direction XR of X-ray emission, the collimator plates 3 and 4 are aligned to intersect respective center positions of detector elements in the channel direction CH. However, the collimator plate 3 or 4 may be aligned to intersect a position offset from the center position of a detector element in the channel direction CH insofar as non-uniformity in detection by the detector elements in the channel direction can be reduced.

Moreover, in the present embodiment, the collimator plate set 2 has the joint layer 5. The joint layer 5 may be formed from any one of various materials insofar as it can join the collimator plates 3 and 4 together. However, the joint layer 5 having a high density gives a poor X-ray use efficiency because X-rays are more easily absorbed. Therefore, it is desirable that the joint layer 5 be formed from a material that can lower the density of the joint layer 5 as much as possible. As an example of implementing a low-density joint layer 5, for example, the bonding sheet 500 may be used, as described in the present embodiment. After adhesively bonding the bonding sheet 500 to the collimator plate 3, the collimator plate 4 is aligned to the collimator plate 3 and the collimator plates 3 and 4 are heated; the bonding sheet 500 then foams by heating, which can form a foam layer between the collimator plates 3 and 4. In the present embodiment, the foam layer is used as the joint layer 5 for joining the collimator plates 3 and 4 together. Since the foam layer contains bubbles, the low-density joint layer 5 can thus be implemented, which makes it possible to enhance X-ray use efficiency.

Moreover, in the present embodiment, the collimator plates 3 and 4 are joined together by heating the bonding sheet 500 to expand. However, the collimator plates 3 and 4 may be joined together by a different method. For example, the collimator plates 3 and 4 may be joined together by: preparing a sheet-like base layer containing a specific material; adhesively bonding one surface of the base layer and the collimator plate 3 together by an adhesive; and adhesively bonding the other surface of the base layer and the collimator plate 4 together by an adhesive. In this case, a combination of the adhesive layers respectively lying between the base layer and collimator plates 3 and 4, together with the base layer constitutes the joint layer 5. For the base layer, a foam layer formed from a foam material, for example, may be used.

It should be noted that the present invention is not limited to the embodiments described above, and several additions, modifications, etc. may be applied.

For example, in the present embodiment, the notches Na to Nd and Ne to Nh are provided on the collimator plates 3 and 4 in each collimator plate set 2, the upper fixing rods 8A to 8D are inserted into the notches Na to Nd and are fixed by an adhesive, and the lower fixing rods 8E to 8H are inserted into the notches Ne to Nh and are fixed by an adhesive. However, the upper fixing rods 8A to 8D may be fixed on the upper edges E1 of the collimator plates 3 and 4 and the lower fixing rods 8E to 8H may be fixed on the lower edges E2 of the collimator plates 3 and 4 without providing the notches Na to Nd and Ne to Nh on the collimator plates 3 and 4. In this case, notches for receiving the upper fixing rods 8A to 8D may be formed in the upper reinforcing plate 9, and those for receiving the lower fixing rods 8E to 8H may be formed in the lower reinforcing plate 10 to sandwich the collimator plate sets 2 between the upper reinforcing plate 9 and lower reinforcing plate 10. Alternatively, no notches may be formed in the upper reinforcing plate 9 and lower reinforcing plate 10, and the collimator plate sets 2 may be sandwiched between the upper reinforcing plate 9 and lower reinforcing plate 10 having no notches.

Moreover, while in the present embodiment, the four upper fixing rods 8A to 8D are used, the number of the upper fixing rods may be more than or less than four, insofar as alignment precision for the collimator plate sets 2 can be adequately retained and the collimator module is given sufficient rigidity. Likewise, the number of the lower fixing rods may be more than or less than four.

Furthermore, in the present embodiment, the collimator module 1 has the upper reinforcing plate 9 and lower reinforcing plate 10. However, the collimator module 1 may be constructed without having at least one of the upper reinforcing plate 9 and lower reinforcing plate 10 insofar as the collimator module 1 can retain sufficient rigidity.

In addition, while in the present embodiment, the upper fixing rods 8A to 8D and lower fixing rods 8E to 8H are fixed to extend in the channel direction CH, which is the direction of arrangement of the collimator plate sets 2, they may be fixed to extend in a direction oblique to the channel direction CH.

Moreover, in the present embodiment, the upper reinforcing plate 9 is formed with the plurality of grooves 92a for inserting thereinto the upper end portions 2c of the plurality of collimator plate sets 2, and the lower reinforcing plate 10 is formed with the plurality of grooves 101a for inserting thereinto the lower end portions 2d of the plurality of collimator plate sets 2. However, a flat reinforcing plate having no grooves may be employed as at least one of the upper reinforcing plate 9 and lower reinforcing plate 10.

Furthermore, in the present embodiment, the surface 6a of the bracket 6 is formed with the slots 6b for receiving therein the front end portions 2a of the collimator plate sets 2 and the surface 7a of the bracket 7 is formed with the slots 7b for receiving therein the rear end portions 2b of the collimator plate sets 2. However, brackets formed with no slots may be employed as the pair of brackets 6 and 7 insofar as they can retain the plurality of collimator plate sets 2.

The present embodiment has addressed the collimator module 1 having the collimator plate sets 2 lined up side by side in the channel direction. However, the present invention is not limited to the collimator module in which the collimator plate sets 2 are lined up side by side in the channel direction, and it can be applied to a collimator module having the collimator plate sets lined up side by side in a direction different from the channel direction. Therefore, the present invention may be applied to a collimator having the collimator plate sets lined up side by side in the slice direction, for example.

Moreover, the present embodiment has addressed a case in which the collimator module 1 is applied to the X-ray CT apparatus 100. However, the collimator module 1 in the present invention may be applied to any radiation tomographic imaging apparatus other than the X-ray CT apparatus that requires the collimator module 1 (e.g., a general X-ray imaging apparatus for imaging a chest or the like, a mammography imaging apparatus for imaging a breast, an angiographic imaging apparatus for contrast-imaging blood vessels, a PET-CT apparatus, or a SPECT-CT apparatus). Furthermore, the collimator module 1 in the present invention may be applied to radiation tomographic imaging apparatuses in a medical field, and in addition, radiographic imaging apparatus (e.g., industrial X-ray apparatus) used in fields different from the medical field.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A collimator module (1) for collimation of X-rays comprising a plurality of collimator plate sets (2) lined up side by side in a channel direction (CH), wherein
  each collimator plate set (2) comprises:
    a first collimator plate (3);
    a second collimator plate (4); and
    a joint layer (5) disposed between said first collimator plate (3) and said second collimator plate (4) for joining said first collimator plate (3) and said second collimator plate (4) together, and
  said plurality of collimator plate sets (2) are lined up side by side in said channel direction (CH) with an air layer (20) intervening between any adjacent two of said plurality of collimator plate sets (2).

2. The collimator module (1) as recited in claim 1, wherein:
  said collimator module (1) is disposed on a side of radiation entrance of a detector (542) having a plurality of detector elements (24) lined up side by side in said channel direction (CH) at first intervals (P3) for detecting the radiation, and
  said plurality of collimator plate sets (2) are aligned to line up side by side in said channel direction (CH) at second intervals (P4), said second interval (P4) being double said first interval (P3).

3. The collimator module (1) as recited in claim 2, wherein: as viewed in a direction (XR) of X-ray radiation emission, said plurality of collimator plate sets (2) are aligned to said detector (542) so that each detector element (24) in said detector (542) has a first region (r1) underlying said joint layer (5) and a second region (r2) underlying said air layer (20).

4. The collimator module (1) as recited in claim 1, wherein: as viewed in a direction (XR) of X-ray emission, the first collimator plate (3) in said collimator plate set (2) is aligned to intersect one (24*c*) of two adjoining detector elements (24*c*, 24*d*), and as viewed in the direction (XR) of X-ray emission, the second collimator plate (4) in said collimator plate set (2) is aligned to intersect the other (24*d*) of said two detector elements (24*c*, 24*d*).

5. The collimator module (1) as recited in claim 4, wherein: as viewed in the direction (XR) of X-ray emission, said first collimator plate (3) is aligned to intersect a center position (m1) of said one detector element (24*c*) in said channel direction (CH), and as viewed in the direction (XR) of X-ray emission, said second collimator plate (4) is aligned to intersect a center position (m2) of said other detector element (24*d*) in said channel direction (CH).

6. The collimator module (1) as recited in claim 1, comprising: a pair of brackets (6, 7) for holding said plurality of collimator plate sets (2).

7. The collimator module (1) as recited in claim 5, comprising:
  a first rod (8A to 8D) adhesively bonded to upper end portions (2*c*) of said collimator plate sets (2); and
  a second rod (8E to 8H) adhesively bonded to lower end portions (2*d*) of said collimator plate sets (2).

8. The collimator module (1) as recited in claim 7, wherein:
  an upper edge and a lower edge of said first collimator plate (3), and an upper edge and a lower edge of said second collimator plate (4) are formed with notches (Na to Nh),
  said first rod (8A to 8D) is received in the notches (Na to Nd) formed on said upper edges, and
  said second rod (8E to 8H) is received in the notches (Ne to Nh) formed on said lower edges.

9. The collimator module (1) as recited in claim 1, comprising:
  a first reinforcing plate (9) covering the upper end portions (2*c*) of said plurality of collimator plate sets (2); and
  a second reinforcing plate (10) covering the lower end portions (2*d*) of said plurality of collimator plate sets (2).

10. The collimator module (1) as recited in claim 1, wherein: said joint layer (5) comprises a foam layer.

11. A radiation detection apparatus comprising a plurality of collimator modules (1) disposed on a side of radiation entrance of a detector (542),
  each collimator module (1) comprising a plurality of collimator plate sets (2) lined up side by side in a channel direction (CH), wherein
  each collimator plate set (2) comprises:
    a first collimator plate (3);
    a second collimator plate (4); and
    a joint layer (5) disposed between said first collimator plate (3) and said second collimator plate (4) for joining said first collimator plate (3) and said second collimator plate (4) together, and
  said plurality of collimator plate sets (2) are lined up side by side in said channel direction (CH) with an air layer (20) intervening between any adjacent two of said plurality of collimator plate sets (2).

12. A method of making a collimator module (1) for collimation of X-rays comprising a plurality of collimator plate sets (2), comprising:

making said plurality of collimator plate sets (2), each collimator plate set (2) comprising: a first collimator plate (3); a second collimator plate (4); and a joint layer (5) disposed between said first collimator plate (3) and said second collimator plate (4) for joining said first collimator plate (3) and said second collimator plate (4) together, and inserting said plurality of collimator plate sets (2) into slots (6*b*, 7*b*) in brackets (6, 7) with an air layer (20) intervening between any adjacent two of said plurality of collimator plate sets (2).

13. The method of making the collimator module (1) as recited in claim 12, wherein: the making said plurality of collimator plate sets (2) comprises:

preparing said first collimator plate (3) and said second collimator plate (4);

adhesively bonding a heat-expansive bonding sheet (500) to a first surface (S1) of said first collimator plate (3);

aligning said second collimator plate (4) to said first collimator plate (3) adhesively bonded with said bonding sheet (500) so that a predetermined gap (G) is kept between a first surface of said second collimator plate (4) and said bonding sheet (500); and heating said bonding sheet (500).

\* \* \* \* \*